US012594170B2

(12) United States Patent
Chaoui et al.

(10) Patent No.: US 12,594,170 B2
(45) Date of Patent: Apr. 7, 2026

(54) COMPUTER-IMPLEMENTED SURGICAL PLANNING BASED ON BONE LOSS DURING ORTHOPEDIC REVISION SURGERY

(71) Applicant: Howmedica Osteonics Corp., Mahwah, NJ (US)

(72) Inventors: Jean Chaoui, Locmaria Plouzané (FR); Sergii Poltaretskyi, Ependes (CH)

(73) Assignee: Howmedica Osteonics Corp., Mahwah, NJ (US)

( * ) Notice: Subject to any disclaimer, the term of this patent is extended or adjusted under 35 U.S.C. 154(b) by 607 days.

(21) Appl. No.: 17/798,763

(22) PCT Filed: Feb. 15, 2021

(86) PCT No.: PCT/US2021/018118

§ 371 (c)(1),
(2) Date: Aug. 10, 2022

(87) PCT Pub. No.: WO2021/167864

PCT Pub. Date: Aug. 26, 2021

(65) Prior Publication Data

US 2023/0113848 A1      Apr. 13, 2023

Related U.S. Application Data

(60) Provisional application No. 62/978,124, filed on Feb. 18, 2020.

(51) Int. Cl.
*A61F 2/46* (2006.01)
*A61B 17/16* (2006.01)
(Continued)

(52) U.S. Cl.
CPC ............... *A61F 2/46* (2013.01); *A61B 34/30* (2016.02); *A61B 17/1684* (2013.01);
(Continued)

(58) Field of Classification Search
CPC ......... A61B 34/10; A61B 34/20; A61B 34/30; A61B 34/35; A61B 34/00; A61B 34/25;
(Continued)

(56) References Cited

U.S. PATENT DOCUMENTS 7,974,677 B2    7/2011  Mire et al.
8,842,893 B2    9/2014  Teichman et al.
(Continued)

FOREIGN PATENT DOCUMENTS

EP        3498197 A2    6/2019
FR        3108419 A1    9/2021
(Continued)

OTHER PUBLICATIONS

Response to Office Action dated Sep. 11, 2023, from counterpart Australian Application No. 2021224529 filed Dec. 21, 2023, 98 pp.
(Continued)

*Primary Examiner* — Marcela I. Shirsat
(74) *Attorney, Agent, or Firm* — Shumaker & Sieffert, P.A.

(57) ABSTRACT

A surgical assistance system may obtain a pre-revision model of a bone of a patient. The pre-revision model of the bone represents a pre-revision state of the bone after a prior orthopedic surgery on the bone. In this example, an orthopedic prosthesis was attached to the bone during the prior orthopedic surgery. Additionally, the surgical assistance system may obtain intra-revision imaging data of the bone. The intra-revision imaging data represents an intra-revision state of the bone during the orthopedic revision surgery after removal of the orthopedic prosthesis from the bone. The surgical assistance system may determine, based on the intra revision imaging data, damaged and intact parts of the bone. The surgical assistance system may then generate a second intra-revision model of the bone by modifying the pre-
(Continued)

revision model of the bone to exclude damaged parts of the bone.

20 Claims, 12 Drawing Sheets

(51) Int. Cl.

| | |
|---|---|
| *A61B 17/17* | (2006.01) |
| *A61B 34/00* | (2016.01) |
| *A61B 34/10* | (2016.01) |
| *A61B 34/20* | (2016.01) |
| *A61B 34/30* | (2016.01) |
| *A61B 90/00* | (2016.01) |
| *A61B 90/50* | (2016.01) |
| *A61F 2/30* | (2006.01) |
| *G02B 27/01* | (2006.01) |

(52) U.S. Cl.
CPC ........... *A61B 17/1778* (2016.11); *A61B 34/10* (2016.02); *A61B 2034/105* (2016.02); *A61B 2034/108* (2016.02); *A61B 34/20* (2016.02); *A61B 2034/2048* (2016.02); *A61B 34/25* (2016.02); *A61B 2034/252* (2016.02); *A61B 2034/258* (2016.02); *A61B 2090/364* (2016.02); *A61B 2090/365* (2016.02); *A61B 90/37* (2016.02); *A61B 2090/371* (2016.02); *A61B 2090/372* (2016.02); *A61B 2090/502* (2016.02); *A61F 2/30* (2013.01); *A61F 2002/30614* (2013.01); *A61F 2002/3069* (2013.01); *A61F 2/4603* (2013.01); *A61F 2/4612* (2013.01); *A61F 2002/4633* (2013.01); *G02B 2027/0138* (2013.01); *G02B 2027/014* (2013.01)

(58) Field of Classification Search
CPC ............ A61B 17/1684; A61B 17/1778; A61B 2017/00207; A61B 2017/00216; A61B 90/37; A61B 2034/105; A61B 2034/108; A61B 2034/2048; A61B 2034/252; A61B 2034/258; A61B 2090/364; A61B 2090/365; A61B 2090/371; A61B 2090/372; A61B 2090/502; A61F 2/46; A61F 2/4603; A61F 2/4612; A61F 2/30; A61F 2002/3069; A61F 2002/4633; A61F 2002/30614; G02B 27/0093; G02B 27/0172; G02B 2027/0138; G02B 2027/014; G02B 2027/0178
USPC ....................................................... 606/86 R
See application file for complete search history.

(56) References Cited

U.S. PATENT DOCUMENTS

| | | | |
|---|---|---|---|
| 8,891,847 | B2 | 11/2014 | Helm et al. |
| 9,675,273 | B2 | 6/2017 | Gluncic |
| 9,808,261 | B2 | 11/2017 | Gelaude et al. |
| 10,172,715 | B2 | 1/2019 | De Wilde et al. |
| 10,194,991 | B2 | 2/2019 | Bonny et al. |
| 10,350,010 | B2 | 7/2019 | Kao et al. |
| 10,405,910 | B2 | 9/2019 | Netravali et al. |
| 10,489,907 | B2 | 11/2019 | Rowley Grant et al. |
| 11,090,019 | B2 | 8/2021 | Siemionow et al. |
| 11,576,725 | B2 | 2/2023 | Chav et al. |
| 2012/0289965 | A1 | 11/2012 | Gelaude et al. |
| 2013/0211531 | A1 | 8/2013 | Steines et al. |
| 2016/0030126 | A1* | 2/2016 | Netravali ............... A61B 17/92 |
| | | | 606/130 |
| 2016/0157751 | A1 | 6/2016 | Mahfouz |
| 2018/0014891 | A1* | 1/2018 | Krebs ................ A61B 17/1703 |
| 2018/0217734 | A1 | 8/2018 | Koenig et al. |
| 2018/0233222 | A1 | 8/2018 | Daley et al. |
| 2019/0175277 | A1 | 6/2019 | Chav et al. |
| 2021/0153946 | A1 | 5/2021 | Bonny et al. |
| 2021/0361357 | A1 | 11/2021 | Crawford |
| 2022/0039868 | A1* | 2/2022 | Chaoui ..................... A61F 2/46 |
| 2023/0056596 | A1 | 2/2023 | Farley et al. |
| 2023/0094903 | A1 | 3/2023 | Harris, Jr. et al. |

FOREIGN PATENT DOCUMENTS

| | | |
|---|---|---|
| KR | 20180044421 A | 5/2018 |
| WO | 2014145591 A2 | 9/2014 |
| WO | 2016094298 A1 | 6/2016 |
| WO | 2016118521 A1 | 7/2016 |
| WO | 2017041080 A1 | 3/2017 |
| WO | 2018013848 A1 | 1/2018 |
| WO | 2019160827 A1 | 8/2019 |
| WO | 2021185940 A1 | 9/2021 |
| WO | 2022046966 A1 | 3/2022 |

OTHER PUBLICATIONS

Notice of Intent to Grant from counterpart Australian Application No. 2021224529 dated Feb. 6, 2024, 3 pp.

Boissonnat et al., "Shape Reconstruction from Planar Cross Sections," Computer Vision, Graphics, and Image Processing, vol. 44, Mar. 29, 1988, 29 pp.

International Preliminary Report on Patentability from International Application No. PCT/US2021/018118 dated Sep. 1, 2022, 9 pp.

International Search Report and Written Opinion of International Application No. PCT/US2021/018118, dated Jun. 4, 2021, 12 pp.

Marker et al., "Contour-Based Surface Reconstruction using Implicit Curve Fitting, and Distance Field Filtering and Interpolation," Volume Graphics, Jan. 2006, 9 pp.

Nguyen et al., "A New Segmentation Method for MRI Images of the Shoulder Joint," Fourth Canadian Conference on Computer and Robot Vision(CRV'07), May 28-30, 2007, 8 pp.

Communication pursuant to Article 94(3) EPC from counterpart European Application No. 21711097.2 dated Feb. 13, 2025, 4 pp.

Office Action from counterpart Australian Application No. 2021224529 dated Sep. 11, 2023, 4 pp.

Response to Communication Pursuant to Rules 161(1) and 162 EPC dated Sep. 27, 2022, from counterpart European Application No. 21711097.2, filed Mar. 17, 2023, 22 pp.

Notice of Intent to Grant and Text Intended to Grant from counterpart European Application No. 21711097.2 dated Jul. 3, 2025, 119 pp.

Response to Communication pursuant to Article 94(3) EPC dated Feb. 13, 2025, from counterpart European Application No. 21711097.2 filed Jun. 11, 2025, 9 pp.

First Examination Report from counterpart Australian Application No. 2024202787 dated Oct. 10, 2025, 6 pp.

Notice of Intent to Grant and Text Intended to Grant from counterpart European Application No. 21711097.2 dated Sep. 24, 2025, 64 pp.

Response to First Examination Report dated Oct. 10, 2025, from counterpart Australian Application No. 2024202787 filed Feb. 16, 2026, 51 pp.

* cited by examiner

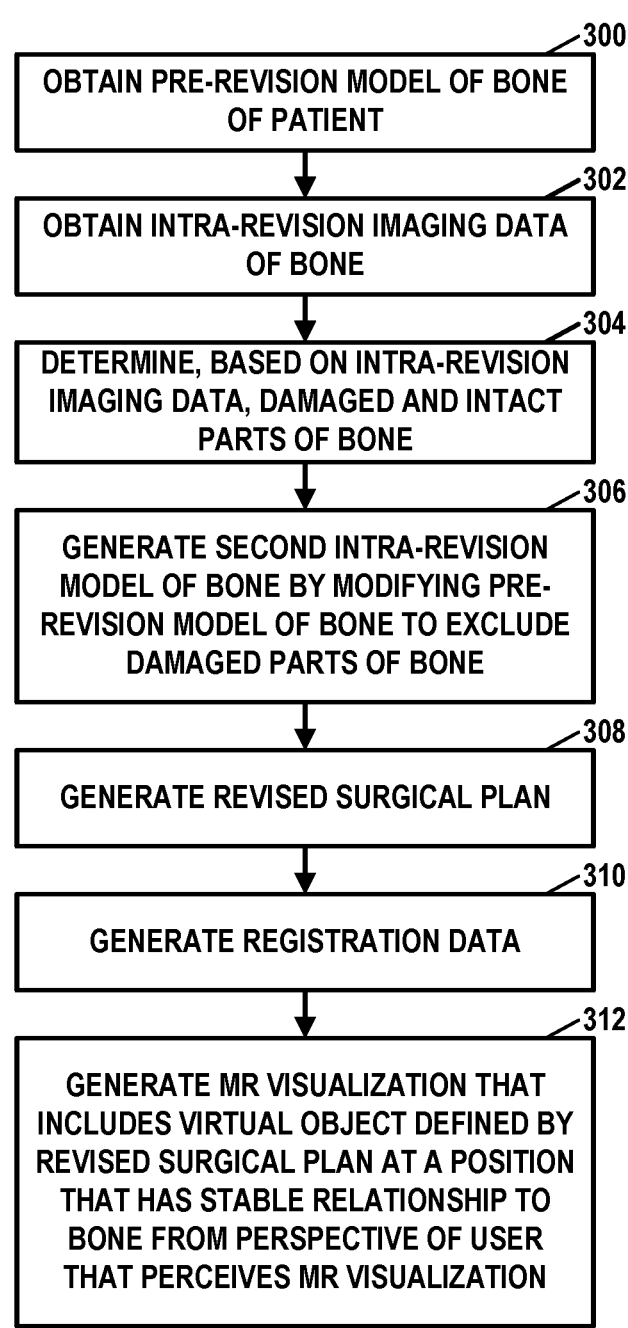

300
OBTAIN PRE-REVISION MODEL OF BONE
OF PATIENT

302
OBTAIN INTRA-REVISION IMAGING DATA
OF BONE

304
DETERMINE, BASED ON INTRA-REVISION
IMAGING DATA, DAMAGED AND INTACT
PARTS OF BONE

306
GENERATE SECOND INTRA-REVISION
MODEL OF BONE BY MODIFYING PRE-
REVISION MODEL OF BONE TO EXCLUDE
DAMAGED PARTS OF BONE

308
GENERATE REVISED SURGICAL PLAN

310
GENERATE REGISTRATION DATA

312
GENERATE MR VISUALIZATION THAT
INCLUDES VIRTUAL OBJECT DEFINED BY
REVISED SURGICAL PLAN AT A POSITION
THAT HAS STABLE RELATIONSHIP TO
BONE FROM PERSPECTIVE OF USER
THAT PERCEIVES MR VISUALIZATION

FIG. 3

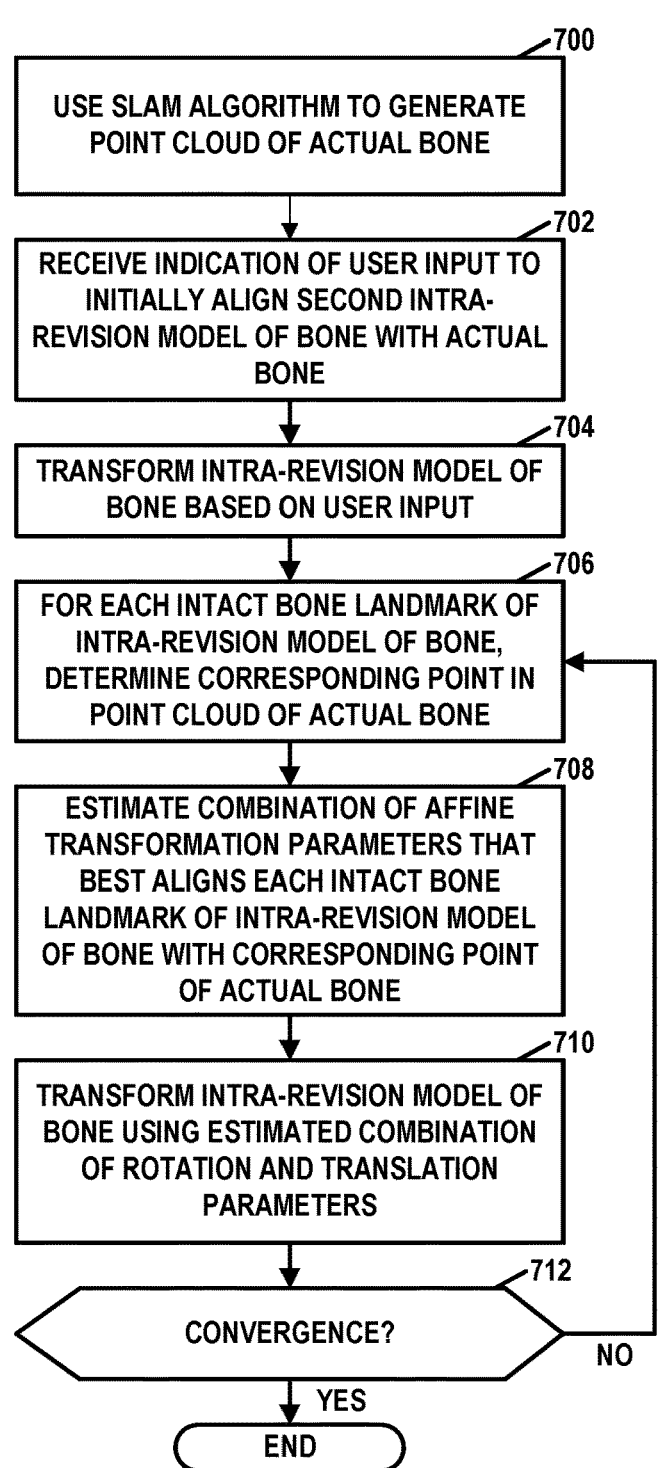

700

USE SLAM ALGORITHM TO GENERATE
POINT CLOUD OF ACTUAL BONE

702

RECEIVE INDICATION OF USER INPUT TO
INITIALLY ALIGN SECOND INTRA-
REVISION MODEL OF BONE WITH ACTUAL
BONE

704

TRANSFORM INTRA-REVISION MODEL OF
BONE BASED ON USER INPUT

706

FOR EACH INTACT BONE LANDMARK OF
INTRA-REVISION MODEL OF BONE,
DETERMINE CORRESPONDING POINT IN
POINT CLOUD OF ACTUAL BONE

708

ESTIMATE COMBINATION OF AFFINE
TRANSFORMATION PARAMETERS THAT
BEST ALIGNS EACH INTACT BONE
LANDMARK OF INTRA-REVISION MODEL
OF BONE WITH CORRESPONDING POINT
OF ACTUAL BONE

710

TRANSFORM INTRA-REVISION MODEL OF
BONE USING ESTIMATED COMBINATION
OF ROTATION AND TRANSLATION
PARAMETERS

712

CONVERGENCE?        NO

YES

END

FIG. 7

COMPUTER-IMPLEMENTED SURGICAL PLANNING BASED ON BONE LOSS DURING ORTHOPEDIC REVISION SURGERY

This application is a national stage application under 35 U.S.C. § 371 of PCT Application No. PCT/US2021/018118, filed Feb. 15, 2021, which claims the benefit of U.S. Provisional Application No. 62/978,124, filed Feb. 18, 2020, the entire content of both of which are incorporated herein by reference.

BACKGROUND

Orthopedic joint repair surgeries involve repair and/or replacement of a damaged or diseased joint. Many times, an orthopedic joint repair surgery, such as joint arthroplasty, involves replacing the damaged joint with a prosthetic that is implanted into the patient's bone. Proper selection and positioning of an orthopedic prosthetic to ensure an optimal surgical outcome can be challenging. To assist with positioning, orthopedic joint repair surgeries often involve the use of surgical instruments to control the shaping of the surface of the damaged bone and cutting or drilling of bone to accept the orthopedic prosthetic.

SUMMARY

This disclosure describes techniques related to performing computer-assisted planning of orthopedic revision surgeries and performing computer-assisted orthopedic revision surgeries. The techniques of this disclosure take into consideration bone loss caused by removal of an existing orthopedic prosthesis during an orthopedic revision surgery. For instance, in one example, a surgical assistance system generates a pre-revision model of a bone. The pre-revision model of the bone represents a state of the bone after a previous orthopedic surgery on the bone and before an orthopedic revision surgery on the bone. Additionally, the surgical assistance system obtains intra-revision imaging data. The intra-revision imaging data of the bone represents a visible portion of the bone during the orthopedic revision surgery after removal of an orthopedic prosthesis previously attached to the bone. Additionally, the surgical assistance system identifies intact and damaged parts of the bone based on the intra-revision imaging data. In this example, the surgical assistance system modifies the pre-revision model of the bone to exclude damaged areas of the bone, thereby generating an intra-revision model of the bone. Thus, in this way, the surgical assistance system may use the intra-operatively obtaining imaging data to generate an intra-revision model of the bone that is updated based on bone loss that occurs during the orthopedic revision surgery. In some examples, the surgical assistance system may then intraoperatively modify a surgical plan for the orthopedic revision surgery based on the intra-revision model of the bone. In some examples, the surgical assistance system may generate a MR visualization that includes a virtual object defined by the revised surgical plan at a position that has a stable spatial relationship to the bone from a perspective of a user that perceives the MR visualization.

In one example, this disclosure describes a computer-implemented method for assisting an orthopedic revision surgery, the method comprising: obtaining a pre-revision model of a bone of a patient, the pre-revision model of the bone representing a pre-revision state of the bone after a prior orthopedic surgery on the bone and before the orthopedic revision surgery, wherein an orthopedic prosthesis was attached to the bone during the prior orthopedic surgery; obtaining intra-revision imaging data of the bone, the intra-revision imaging data representing an intra-revision state of the bone during the orthopedic revision surgery after removal of the orthopedic prosthesis from the bone; determining, based on the intra-revision imaging data, damaged and intact parts of the bone; and generating a second intra-revision model of the bone by modifying the pre-revision model of the bone to exclude damaged parts of the bone.

In another example, this disclosure describes a computing system for assisting an orthopedic revision surgery comprising: a storage system configured to store a pre-revision model of the bone, the pre-revision model of the bone representing a pre-revision state of the bone after a prior orthopedic surgery on the bone and before the orthopedic revision surgery, wherein an orthopedic prosthesis was attached to the bone during the prior orthopedic surgery; and one or more processing circuits configured to: obtain intra-revision imaging data of the bone, the intra-revision imaging data representing an intra-revision state of the bone during the orthopedic revision surgery after removal of the orthopedic prosthesis from the bone; determine, based on the intra-revision imaging data, damaged and intact parts of the bone; and generate a second intra-revision model of the bone by modifying the pre-revision model of the bone to exclude damaged parts of the bone.

The details of various examples of the disclosure are set forth in the accompanying drawings and the description below. Various features, objects, and advantages will be apparent from the description, drawings, and claims.

BRIEF DESCRIPTION OF DRAWINGS

FIG. 3 is a flowchart illustrating an example operation of the surgical assistance system, in accordance with one or more techniques of this disclosure.

FIG. 7 is a flowchart illustrating an example operation of the surgical assistance system to register an intra-revision model of the bone with the actual, real-world bone of a patient, in accordance with one or more techniques of this disclosure.

DETAILED DESCRIPTION

Figure 1:
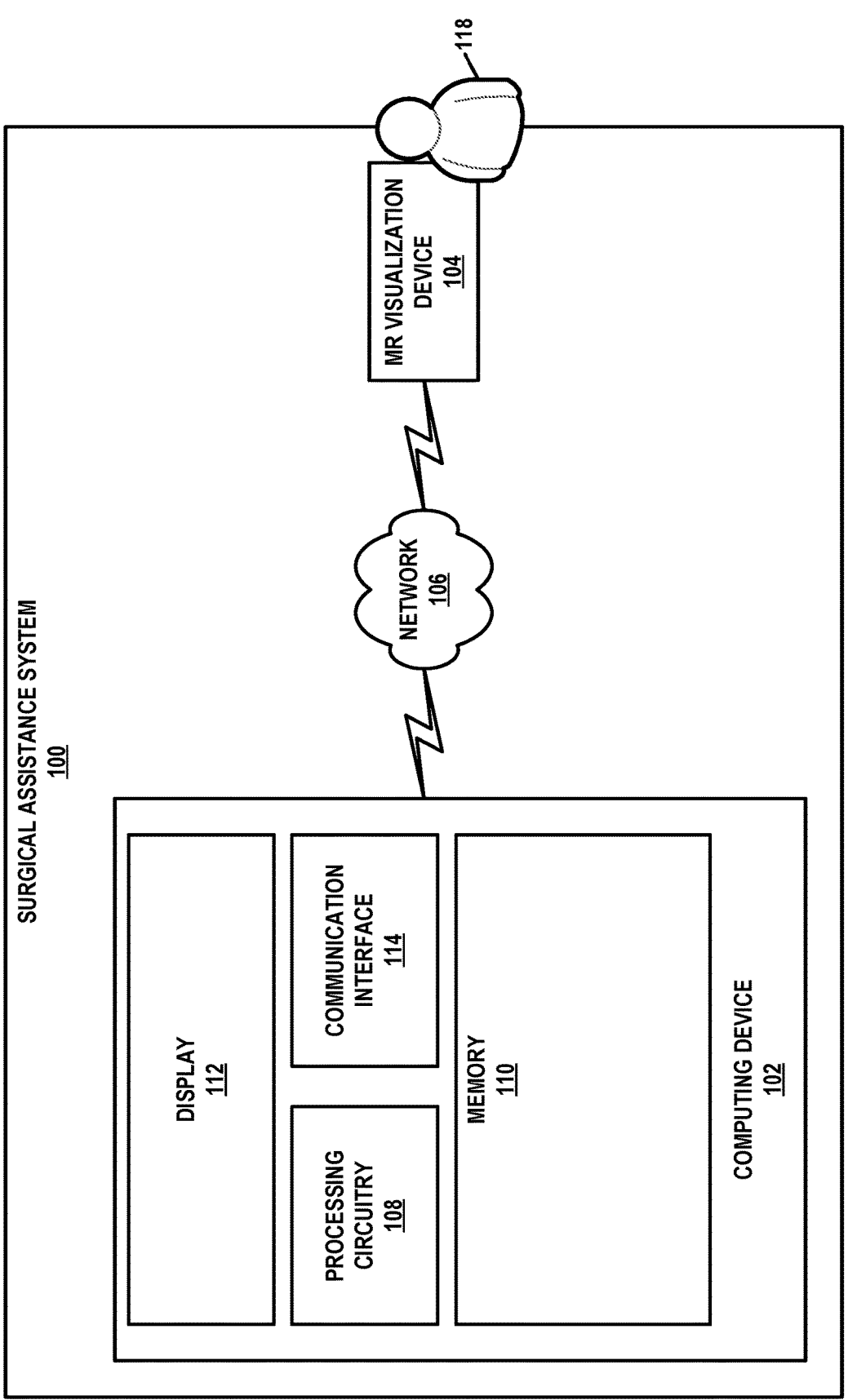
FIG. 1 is a block diagram illustrating an example surgical assistance system that may be used to implement one or more techniques of this disclosure.

An orthopedic revision surgery is an orthopedic surgery on a surgical site that has previously been the subject of an earlier orthopedic surgery. For example, a glenoid prosthesis may have been attached to a glenoid of a scapula of a patient during an earlier orthopedic surgery. In this example, the glenoid prosthesis may have failed, reached the end of its useful life, is causing discomfort to the patient, or otherwise requires revision, e.g., including modification and/or replacement. Accordingly, in this example, a surgeon may perform an orthopedic revision surgery to remove and replace, or otherwise modify, the glenoid prosthesis.

Removal of an orthopedic prosthesis during an orthopedic revision surgery may result in the loss of bone that was present prior to removal of the orthopedic prosthesis. For instance, in an example where the orthopedic prosthesis is a glenoid prosthesis, an intact portion of the scapula may break away with the glenoid prosthesis when the glenoid prosthesis is removed from the scapula. Such bone loss may occur because many orthopedic prostheses are designed to allow bone to naturally grow into the orthopedic prostheses. While it can be anticipated that bone loss may occur when removing an orthopedic prosthesis during an orthopedic revision surgery, it may be difficult to predict before the orthopedic revision surgery exactly where such bone loss will occur and how much bone loss will occur.

Because it may be difficult to predict before the orthopedic revision surgery exactly where such bone loss will occur and how much bone loss will occur, a surgeon may need to update a surgical plan for the orthopedic revision surgery during the course of the orthopedic revision surgery. For example, the amount or location of bone loss caused by removal of an existing orthopedic prosthesis may require the surgeon to use a differently sized orthopedic prosthesis. In another example, the amount or location of bone loss caused by removal of an existing orthopedic prosthesis may require the surgeon to perform one or more previously unplanned bone grafts and/or attach a replacement orthopedic prosthesis to the bone in a manner that is different from a manner set forth in a previously determined plan for the orthopedic revision surgery. In another example, the amount or location of bone loss caused by removal of an existing orthopedic prosthesis may make it beneficial for, or may require, a robot to perform cuts or drill holes in bones at different positions and/or angles. Thus, problems may arise with respect to how to modify a plan for an orthopedic revision surgery to account for bone loss caused by removal of an existing orthopedic prosthesis during the orthopedic revision surgery. If not done properly, modifying a surgical plan during surgery is challenging and may lead to errors.

Today, visualization tools are available to surgeons that use three-dimensional modeling of bone shapes to facilitate preoperative planning for joint repairs and replacements. These tools can assist surgeons with customizing a surgical plan for each patient. For example, mixed reality (MR)-assisted surgery is quickly becoming a reality in operating rooms. In some forms of MR-assisted surgery, a MR visualization device presents an MR visualization that includes one or more virtual objects that have stable spatial relationships with respect to real-world objects from the perspective of a user that perceives the MR visualization. Example virtual objects may include 3-dimensional (3D) models of a bone, 3D objects representing drilling axes or cutting planes, and so on. Thus, in one example, a 3D model of a bone may appear to the user to remain superimposed on an actual bone of the patient, regardless of whether the user looks away from the bone or whether the user changes position.

Registration is an important part of maintaining stable spatial relationships between virtual objects and real-world objects. At a basic level, registration is a process of determining a transformation function that maps points in a coordinate system of the virtual objects to points in a coordinate system for real-world objects. In some examples where an MR system is registering a real-world bone of a patient with a 3D model of the bone, the MR system may identify coordinates for landmark locations on the real-world bone. In such examples, an MR system may match the coordinates for the landmark locations on the real-world bone to coordinates of corresponding points on the 3D model of the bone. For example, the MR system may identify coordinates for various points along a rim of a glenoid cavity of a scapula of the patient. In this example, the MR system may match the coordinates for the points along the rim of the glenoid cavity of the scapula to corresponding points on a virtual model of the scapula. In general, this process relies on the 3D model of the bone essentially matching the actual bone of the patient.

If there is bone loss caused by the removal of an existing orthopedic prosthesis during an orthopedic revision surgery, the 3D model of a bone generated before the removal of the existing orthopedic prosthesis does not match the real-word bone of the patient. Rather, some of the landmark locations on the real-world bone may be lost during removal of the existing orthopedic prosthesis. For example, various parts of the rim of the glenoid cavity may be lost during removal of the existing orthopedic prosthesis. The mismatch between the real-world bone and the 3D model of the bone may make it difficult for an MR system to register the real-world bone and the 3D model of the bone. For instance, it may be difficult to determine corresponding points on the real-world bone and the 3D model of the bone when the 3D model of the bone includes points that correspond to parts of the real-world bone that were lost during removal of the existing orthopedic prosthesis. Thus, a problem may arise in how register a 3D model of a bone with a real-world bone after removal of an orthopedic prosthesis from the bone.

This disclosure describes techniques for intra-operatively updating surgical plans for orthopedic revision surgeries and techniques for MR guidance in orthopedic revision surgeries. The techniques of this disclosure may provide solutions to one or more of the problems described above. In one example, this disclosure describes a surgical assistance system configured to generate a pre-revision model of a bone of a patient. The pre-revision model of the bone represents a pre-revision state of the bone after a prior orthopedic surgery on the bone and before the orthopedic revision surgery. An orthopedic prosthesis may have been attached to the bone during the prior orthopedic surgery. Additionally, the surgical assistance system may obtain intra-revision imaging data of the bone. The intra-revision imaging data represents an intra-revision state of the bone during the orthopedic revision surgery after removal of the orthopedic prosthesis from the bone. The surgical assistance system may determine, based on the intra-revision imaging data, damaged and intact parts of the bone. Subsequently, the surgical assistance system may generate an intra-revision model of the bone by modifying the pre-revision model of the bone to exclude the damaged parts of the bone. The surgical assistance system may generate a revised surgical plan for the orthopedic revision surgery based on the intra-revision model of the bone.

By identifying damaged and intact parts of the bone, modifying the pre-revision model of the bone to generate a second intra-revision model of the bone, e.g., based on the identified parts, and using the second intra-revision model of the bone as a basis for generating a revised surgical plan, the surgical assistance system may be better able to generate the revised surgical plan, as compared to surgical assistance systems that do not have access to an intra-revision model of the bone after removal of the orthopedic appliance from the bone. Moreover, in some examples, the surgical assistance system may generate a MR visualization that includes a virtual object defined by the revised surgical plan at a position that has a stable spatial relationship to the bone from a perspective of a user that perceives the MR visualization, wherein the virtual object provides information to the user about the orthopedic revision surgery. Because the second intra-revision model of the bone excludes damaged portions of the bone, it may be easier to register the second intra-revision model of the bone with the actual bone of the patient after removal of the orthopedic prosthesis from the bone, as compared to trying to register the pre-revision model of the bone with the actual bone of the patient after removal of the orthopedic prosthesis from the bone.

FIG. 1 is a block diagram illustrating an example surgical assistance system 100 that may be used to implement one or more techniques of this disclosure. Surgical assistance system 100 includes a computing device 102, a MR visualization device 104, and a network 106. In other examples, surgical assistance system 100 may include more or fewer devices or systems. For instance, in some examples, tasks performed by computing device 102 may be performed by MR visualization device 104. In other examples, tasks described in this disclosure as being performed by computing device 102 may be performed by a system of multiple computing devices. Furthermore, in some examples, surgical assistance system 100 may include multiple MR visualization devices or may include no MR visualization devices. In some examples, surgical assistance system 100 does not include network 106.

Computing device 102 of surgical assistance system 100 may include various types of computing devices, such as server computers, personal computers, smartphones, laptop computers, and other types of computing devices. In the example of FIG. 1, computing device 102 includes processing circuitry 108, memory 110, display 112, and a communication interface 114. Display 112 is optional, such as in examples where computing device 102 comprises a server computer.

Examples of processing circuitry 108 include one or more microprocessors, digital signal processors (DSPs), application specific integrated circuits (ASICs), field programmable gate arrays (FPGAs), hardware, or any combinations thereof. In general, processing circuitry 108 may be implemented as fixed-function circuits, programmable circuits, or a combination thereof. Fixed-function circuits refer to circuits that provide particular functionality and are preset on the operations that can be performed. Programmable circuits refer to circuits that can be programmed to perform various tasks and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits.

Processing circuitry 108 may include arithmetic logic units (ALUs), elementary function units (EFUs), digital circuits, analog circuits, and/or programmable cores, formed from programmable circuits. In examples where the operations of processing circuitry 108 are performed using software executed by the programmable circuits, memory 110 may store the object code of the software that processing circuitry 108 receives and executes, or another memory within processing circuitry 108 (not shown) may store such instructions. Examples of the software include software designed for surgical planning. Processing circuitry 108 may perform the actions ascribed in this disclosure to surgical assistance system 100.

Memory 110 may store various types of data used by processing circuitry 108. For example, memory 110 may store data describing 3D models of various anatomical structures, including morbid and predicted premorbid anatomical structures. For instance, in one specific example, memory 110 may store data describing a 3D model of a humerus of a patient, imaging data, and other types of data.

Memory 110 may be formed by any of a variety of memory devices, such as dynamic random access memory (DRAM), including synchronous DRAM (SDRAM), magnetoresistive RAM (MRAM), resistive RAM (RRAM), or other types of memory devices. Examples of display 112 may include a liquid crystal display (LCD), a plasma display, an organic light emitting diode (OLED) display, or another type of display device.

Communication interface 114 of computing device 102 allows computing device 102 to output data and instructions to and receive data and instructions from MR visualization device 104 via network 106. Communication interface 114 may be hardware circuitry that enables computing device 102 to communicate (e.g., wirelessly or using wires) to other computing systems and devices, such as MR visualization device 104. Network 106 may include various types of communication networks including one or more wide-area networks, such as the Internet, local area networks, and so on. In some examples, network 106 may include wired and/or wireless communication links.

MR visualization device 104 may use various visualization techniques to display MR visualizations to a user 118, such as a surgeon, nurse, technician, or other type of user. A MR visualization may comprise one or more virtual objects that are viewable by a user at the same time as real-world objects. Thus, what the user sees is a mixture of real and virtual objects. It is noted that user 118 does not form part of surgical assistance system 100.

MR visualization device 104 may comprise various types of devices for presenting MR visualizations. For instance, in some examples, MR visualization device 104 may be a Microsoft HOLOLENS™ headset, such as the HOLOLENS 2 headset, available from Microsoft Corporation, of Redmond, Washington, USA, or a similar device, such as, for example, a similar MR visualization device that includes waveguides. The HOLOLENS™ device can be used to present 3D virtual objects via holographic lenses, or wave-guides, while permitting a user to view actual objects in a real-world scene, i.e., in a real-world environment, through the holographic lenses. In some examples, MR visualization device 104 may be a holographic projector, head-mounted smartphone, special-purpose MR visualization device, or other type of device for presenting MR visualizations. In some examples, MR visualization device 104 includes a head-mounted unit and a backpack unit that performs at least some of the processing functionality of MR visualization device 104. In other examples, all functionality of MR visualization device 104 is performed by hardware residing in a head-mounted unit.

MR visualization device 104 may use visualization tools that are available to utilize patient image data to generate 3D models of bone contours to facilitate preoperative planning for joint repairs and replacements. These tools allow surgeons to design and/or select surgical guides and implant components that closely match the patient's anatomy. These tools can improve surgical outcomes by customizing a surgical plan for each patient. An example of such a visualization tool for joint repair surgeries is the BLUEPRINT™ system available from Wright Medical Technology, Inc. The BLUEPRINT™ system provides the surgeon with two-dimensional planar views of the joint-repair region as well as a three-dimensional virtual model of the joint-repair region. The surgeon can use the BLUEPRINT™ system to select, design or modify appropriate orthopedic prostheses, determine how best to position and orient the orthopedic prostheses, how to shape the surface of bones to receive the orthopedic prostheses, and how design, select or modify surgical guide tool(s) or instruments to carry out a surgical plan. The information generated by the BLUEPRINT™ system may be compiled in a preoperative surgical plan for the patient that is stored in a database at an appropriate location (e.g., on a server in a wide area network, a local area network, or a global network) where it can be accessed by the surgeon or other care provider, including before and during the actual surgery.

Discussion in this disclosure of actions performed by surgical assistance system 100 may be performed by one or more computing devices (e.g., computing device 102) of surgical assistance system 100, MR visualization device 104, or a combination of the one or more computing devices and MR visualization device 104.

User 118 may use surgical assistance system 100 during a preoperative phase of an orthopedic revision surgery and an intraoperative phase of the orthopedic revision surgery. The preoperative phase of the orthopedic revision surgery may occur after a prior orthopedic surgery on a patient and before an orthopedic revision surgery on the same surgical site of the same patient. The intraoperative phase of the orthopedic revision surgery occurs during performance of the orthopedic revision surgery.

During the preoperative phase of the orthopedic revision surgery, surgical assistance system 100 may generate a pre-revision model of a bone involved in the orthopedic revision surgery. The pre-revision model of the bone may be a 3-dimensional virtual model of the bone. Surgical assistance system 100 may generate the pre-revision model based on pre-revision imaging data, such as CT scans, x-ray images, ultrasonic imaging, and other types of imaging data generated during or after a prior orthopedic surgery and before an orthopedic revision surgery. For instance, in some examples, surgical assistance system 100 may use image processing and segmentation operations to identify bone structures within the pre-revision imaging data.

Furthermore, during the preoperative phase of the ortho-pedic revision surgery, user 118 may use MR visualization device 104 or another type of device to view the pre-revision model of the bone. For ease of explanation, this disclosure assumes that user 118 uses MR visualization device 104 to interact with surgical assistance system 100 during the preoperative phase. However, it will be understood that user 118 may use other devices, such as a personal computer, tablet computer, or other type of device to interact with surgical assistance system 100 during the preoperative phase. Viewing the pre-revision model of the bone may help user 118 understand the shape and other characteristics of the bone.

In some examples, surgical assistance system 100 may identify an existing orthopedic prosthesis attached to the bone (e.g., based on pre-revision imaging data, medical records, and/or other types of information) and generate a 3-dimensional (3D) virtual model of the existing orthopedic prosthesis. Additionally, surgical assistance system 100 may identify, based on the pre-revision model of the bone, one or more of a replacement orthopedic prosthesis, attachment points for the replacement orthopedic prosthesis, surgical items to use in the orthopedic revision surgery, cutting planes to use during the orthopedic revision surgery, drilling or reaming axes to use during the orthopedic revision surgery, and other aspects of the orthopedic revision surgery. Surgical assistance system 100 may identify such aspects of the orthopedic revision surgery using one or more of an artificial neural network, a set of predefined rules, or other computer-implemented processes.

During the preoperative phase of the orthopedic revision surgery, MR visualization device 104 may generate output (e.g., MR visualizations) that contains 3-dimensional virtual objects in addition to the pre-operative mode of the bone that represent various aspects of the orthopedic revision surgery. For example, the 3-dimensional virtual objects may include virtual objects representing cutting planes, drilling axes, reaming axes, and so on. As part of planning the orthopedic revision surgery, user 118 may be able to change a plan for the orthopedic revision surgery by providing input to sur-gical assistance system 100 to manipulate one or more of the virtual objects. For example, surgical assistance system 100 may change the plan for the orthopedic revision surgery in response to an indication of user input to change a position of a virtual object representing a drilling axis. In another example, the initial plan for the orthopedic revision surgery may be based on a belief that the patient's glenoid belongs to a specific class in a classification system, such as a Walch classification system. In this example, surgical assistance system 100 may change the plan for the orthopedic revision surgery in response to an automatic or manual determination that the patient's glenoid belongs to a different class in the classification system.

Certain 3D virtual objects have fixed spatial relationships with one another, even if the MR visualization does not include each of the 3D virtual objects concurrently. For example, surgical assistance system 100 may generate a first 3D virtual object that includes a 3D model of a pre-revision state of a bone of a patient (i.e., a pre-revision model). In this example, surgical assistance system 100 may also generate a second 3D virtual object that includes a cylinder that represents a drilling axis along which user 118 is to drill into the bone during an orthopedic surgery. In this example, the first and second 3D virtual objects have a fixed spatial relationship to one another in a coordinate system. However, during the preoperative and intraoperative phases of the orthopedic revision surgery there may be times when user 118 wants the MR visualization presented by MR visualization device 104 to include the first virtual object and not the second virtual object, times when user 118 wants the MR visualization to include the second virtual object and not the first virtual object, times when user 118 wants the MR visualization to include both the first and second virtual object, and times when user 118 wants the MR visualization to include neither the first nor second virtual objects. For instance, user 118 may want to see the 3D model of the bone during the preoperative phase of the orthopedic surgery, but not while user 118 is actually drilling a hole into the bone along the drilling axis represented by the cylinder of the second virtual object.

As described this disclosure, user 118 may wear MR visualization device 104 during an orthopedic surgery, such as an orthopedic revision surgery. An MR visualization presented by MR visualization device 104 to user 118 may include virtual objects that are designed to help user 118 perform the orthopedic surgery. For example, the MR visualization may include text that reminds user 118 to perform particular actions at particular stages of the orthopedic surgery. In some examples, the MR visualization may include 3D virtual objects that represent cutting planes, drilling axes, reaming axes, virtual bones, and so on.

In order to assist user 118 in performing the orthopedic revision surgery, it may be necessary to ensure that the virtual objects accurately indicate what user 118 should do, given the bone loss that may occur when the existing orthopedic prosthesis is removed. For instance, it may be inappropriate to use a replacement orthopedic prosthesis specified by a surgical plan for the orthopedic revision surgery if use of the replacement orthopedic prosthesis would cause further damage, given the bone loss caused by removal of the existing orthopedic prosthesis. In another example, it may be inappropriate to use a replacement orthopedic prosthesis at a location specified by a surgical plan for the orthopedic prosthesis if the replacement orthopedic prosthesis is no longer attachable at the location specified by the surgical plan or no longer attachable at the location specified by the surgical plan without a bone graft. Thus, it may be advantageous to revise the surgical plan for the orthopedic revision surgery during the course of the orthopedic revision surgery (e.g., to change which orthopedic prosthesis to use).

Additionally, in order to assist user 118 in performing the orthopedic revision surgery, it may be desirable to ensure that the virtual objects are correctly aligned with real anatomic features of the patient. For instance, in an example where a virtual object represents a drilling axis for a hole to be drilled into a real bone of the patient, it may be important for the drilling axis to have a correct 3-dimensional position with respect to the bone. Accordingly, surgical assistance system 100 may perform a registration process that determines a spatial relationship between virtual objects and real-world objects. In other words, by performing the registration process, surgical assistance system 100 may generate registration data that describes a spatial relationship between one or more virtual objects and real-world objects. The registration data may express a transformation function that maps a coordinate system of the virtual objects to a coordinate system of the real-world objects. In some examples, the registration data is expressed in the form of a transform matrix that, when multiplied by a coordinate of a point in the coordinate system of the real-world objects, results in a coordinate of a point in the coordinate system of the virtual objects.

As part of performing the registration process, surgical assistance system 100 may generate a first point cloud and a second point cloud. The first point cloud includes points corresponding to landmarks on one or more virtual objects, such as a pre-revision model of a bone. The second point cloud includes points corresponding to landmarks on real-world objects. Landmarks may be locations on virtual or real-world objects. The points in the first point cloud may be expressed in terms of coordinates in a first coordinate system and the points in the second point cloud may be expressed in terms of coordinates in a second coordinate system. Because the virtual objects may be designed with positions that are relative to one another but not relative to any real-world objects, the first and second coordinate systems may be different.

Surgical assistance system 100 may generate the second point cloud using a Simultaneous Localization and Mapping (SLAM) algorithm. By performing the SLAM algorithm, surgical assistance system 100 may generate the second point cloud based on observation data generated by sensors of MR visualization device 104 while also tracking allocation of MR visualization device 104. Surgical assistance system 100 may perform one of various implementations of SLAM algorithms, such as a SLAM algorithm having a particular filter implementation, an extended Kalman filter implementation, a covariance intersection implementation, a GraphSLAM implementation, an ORB SLAM implementation, or another implementation. In accordance with some examples of this disclosure, surgical assistance system 100 may apply an outlier removal process to remove outlying points in the first and/or second point clouds. In some examples, the outlying points may be points lying beyond a certain standard deviation threshold from other points in the point clouds. Applying outlier removal may improve the accuracy of the registration process.

Furthermore, as part of performing the registration process during an orthopedic surgery, the MR visualization presented by MR visualization device 104 may include a starting-point virtual object. The starting-point virtual object may be a virtual object that corresponds to a real-world object visible to user 118. For example, during an orthopedic surgery in which a particular bone of a patient is exposed, the starting-point virtual object may include a 3D model of the particular bone. Additionally, MR visualization device 104 may receive an indication of user input to position the starting-point virtual object such that the starting-point virtual object is generally at a position of the corresponding real-world object. For instance, MR visualization device 104 may receive an indication of user input to position the 3D model of the particular bone onto the particular, real-world bone of the patient. Positioning the starting-point virtual object onto the corresponding real-world object may enable MR visualization device 104 to determine a preliminary spatial relationship between points in the first point cloud and points in the second point cloud. The preliminary spatial relationship may be expressed in terms of translational and rotational parameters.

Next, surgical assistance system 100 may refine the preliminary spatial relationship between points in the first point cloud and points in the second point cloud. For example, MR visualization device 104 may perform an iterative closest point (ICP) algorithm to refine the preliminary spatial relationship between the points in the first point cloud and the points in the second point cloud. The iterative closest point algorithm finds a combination of translational and rotational parameters that minimize the sum of distances between corresponding points in the first and second point clouds. For example, consider a basic example where landmarks corresponding to points in the first point cloud are at coordinates A, B, and C and the same landmarks correspond to points in the second point cloud are at coordinates A', B', and C'. In this example, the iterative closest point algorithm determines a combination of translational and rotational parameters that minimizes $\Delta A + \Delta B + \Delta C$, where $\Delta A$ is the distance between A and A', $\Delta B$ is the distance between B and B', and $\Delta C$ is the distance between C and C'. To minimize the sum of distances between corresponding landmarks in the first and second point clouds, surgical assistance system 100 may perform following steps:

1. For each point of the first point cloud, determine a corresponding point in the second point cloud. The corresponding point may be a closest point in the second point cloud. In this example, the first point cloud includes points corresponding to landmarks on one or more virtual objects and the second point cloud may include points corresponding to landmarks on real-world objects.
2. Estimate a combination of rotation and translation parameters using a root mean square point-to-point distance metric minimization technique that best aligns each point of the first point cloud to its corresponding point in the second point cloud.
3. Transform the points of the first point cloud using the estimated combination of rotation and translation parameters.
4. Iterate steps 1-3 using the transformed points of the first point cloud.

In this example, after performing an appropriate number of iterations, surgical assistance system 100 may determine rotation and translation parameters that describe a spatial relationship between the original positions of the points in the first point cloud and the final positions of the points in the first point cloud. The determined rotation and translation parameters can therefore express a mapping between the first point cloud and the second point cloud.

As noted above, the iterative closest point algorithm includes a step of determining, for each point of the first point cloud, a corresponding point in the second point cloud. For instance, in an example where the first point cloud includes points corresponding to landmarks on a virtual model of a humerus, the first point cloud may include a point that corresponds to a most-medial point of the head of the virtual model of the humerus. In this example, the corresponding point in the second point cloud may correspond to the real-world most-medial point on the head of the real-world humerus of a patient. However, if the iterative closest point algorithm does not correctly determine a point in the second point cloud that corresponds to a point in the first point cloud, the registration process may potentially produce inaccurate rotation and translation parameters. Similarly, if a point in the first cloud corresponds to a landmark in a virtual object and there is no corresponding landmark on a corresponding real-world object, the registration process may potentially produce inaccurate rotation and translation parameters. Thus, it may be desirable to have the starting-point virtual object match the corresponding real-world object as closely as possible.

The techniques of this disclosure may address this issue. Accordingly, surgical assistance system 100 may obtain a pre-revision model of a bone of the patient. The pre-revision model of the bone represents a pre-revision state of the bone after a prior orthopedic surgery on the bone and before the orthopedic revision surgery, wherein an orthopedic prosthesis was attached to the bone during the prior orthopedic surgery. In some examples, surgical assistance system 100 may obtain the pre-revision model from a remote or local data storage system.

In some examples, surgical assistance system 100 may generate the pre-revision model of the bone based on pre-revision imaging data. The pre-revision model of the bone may include the first point cloud (i.e., a point cloud that includes points corresponding to landmarks on one or more virtual objects). Surgical assistance system 100 may obtain pre-revision imaging data during a preoperative planning phase of an orthopedic revision surgery. For instance, surgical assistance system 100 may retrieve the pre-revision imaging data from a data storage system, receive the pre-revision imaging data from an imaging device, or otherwise receive or generate the pre-revision imaging data. The pre-revision imaging data may represent a pre-revision state of a bone after a prior orthopedic surgery and before the orthopedic revision surgery. For example, the pre-revision imaging system may include computed tomography (CT) images captured after the prior orthopedic surgery and before the orthopedic revision surgery, images captured during the prior orthopedic surgery, or other types of imaging data.

As noted above, surgical assistance system 100 may use the pre-revision imaging data to generate a 3D model of the pre-revision state of the bone. Thus, the 3D model of the pre-revision state of the bone represents what user 118 may expect the bone to be immediately before starting the orthopedic revision surgery. Because the 3D model of the pre-revision state of the bone is based on imaging data generated after the prior orthopedic surgery and before the orthopedic revision surgery, the 3D model of the pre-revision state of the bone may closely match the real-world pre-revision state of the bone. Thus, the 3D model of the pre-revision state of the bone may serve as a good starting-point virtual object during a registration process. As part of generating the 3D model of the pre-revision state of the bone, surgical assistance system 100 may generate an initial pre-revision model of the bone and identify borders of an existing orthopedic prosthesis attached to the bone. Surgical assistance system 100 may modify the pre-revision model of the bone to exclude areas occupied by the existing orthopedic prosthesis. Because orthopedic prostheses are typically more radiopaque than bone, surgical assistance system 100 may use edge detection in radiographic images of the bone to detect the borders of the existing orthopedic prosthesis. Edge detection may involve detection of differences in intensity values of linearly arranged pixels of a radiographic image that exceed one or more thresholds.

As noted elsewhere in this disclosure, bone loss may occur during orthopedic revision surgeries when a surgeon (e.g., user 118) removes an existing orthopedic prosthesis attached to a bone. For instance, in an example where the surgeon is performing an orthopedic revision surgery to revise a previously performed partial or total shoulder arthroplasty, the surgeon may remove a glenoid prosthesis that is attached to a scapula of the patient. In this example, parts of the scapula may come away with the glenoid prosthesis when the surgeon removes the glenoid prosthesis from the scapula. Because of the bone loss that occurs when the surgeon removes the orthopedic prosthesis from a bone, an intra-revision state of the bone may be different from the pre-revision state of the bone. The intra-revision state of the bone is a state of the bone during the orthopedic revision surgery after removal of the orthopedic prosthesis from the bone. Because the intra-revision state of the bone is different from the pre-revision state of the bone, some parts of the 3D model of the pre-revision state of the bone may not be accurate with respect to the intra-revision state of the bone. Thus, when surgical assistance system 100 attempts to perform the registration process after removal of the ortho-pedic prosthesis, surgical assistance system 100 may be unable to accurately determine landmarks on the bone that correspond to landmarks in the 3D model of the pre-revision state of the bone. As a result, the transform produced by the registration process may not be sufficiently accurate. With-out sufficient accuracy in the transform, user 118 would not be able to use various drilling axes, cutting planes, reaming axes, etc. represented by other virtual objects as guides when performing later steps of the orthopedic revision surgery. Furthermore, in some examples where the surgeon is using MR visualization device 104 during the orthopedic revision surgery and MR visualization device 104 presents a 3D model of the bone, the 3D model of the pre-revision state of the bone may no longer accurately represent the intra-revision state of the bone due to bone loss caused by removal of the previous orthopedic prosthesis.

Techniques of this disclosure may improve intra-opera-tive planning of orthopedic revision surgeries and/or improve the accuracy of the transform produced by the registration process. The improvements to the accuracy of the transform produced by the registration process may increase the ability of surgical assistance system 100 to maintain stable spatial relationships between virtual objects and real world objects, thus potentially enabling user 118 to use various virtual objects as guides when performing particular steps of an orthopedic revision surgery. As part of performing the techniques of this disclosure, surgical assis-tance system 100 may obtain intra-revision imaging data during an orthopedic revision surgery. The intra-revision imaging data represents an intra-revision state of the bone during the orthopedic revision surgery after removal of an orthopedic prosthesis from the bone. The intra-revision imaging data may comprise one or more types of imaging data. For example, the intra-revision imaging data may comprise RGB image data, stereoscopic RGB image data, depth image data, CT imaging data, and/or other types of imaging data.

Surgical assistance system 100 may then determine, based on the intra-revision imaging data, damaged and intact parts of the bone. The damaged parts of the bone may include parts of the bone that are different in the intra-revision state of the bone from a pre-morbid state of the bone. The intact parts of the bone are parts of the bone that are the same in the intra-revision state of the bone and the pre-morbid state of the bone.

In some examples, to determine the damaged and intact parts of the bone based on the intra-revision imaging data of the bone, surgical assistance system 100 may generate, based on the intra-revision imaging data, a first intra-revision model of the bone. The first intra-revision model of the bone may be or may comprise a point cloud representing relative positions in 3D space of points on the bone and surrounding tissue. Because some tissue (e.g., muscle, skin, etc.) covers some portions of the bone, the first intra-revision model of the bone may not include points corresponding to all portions of the bone, or all portions of the bone repre-senting in the pre-revision model of the bone. In some examples, surgical assistance system 100 may use the intra-revision imaging data in a SLAM algorithm to generate the first intra-revision model of the bone. Furthermore, in some such examples, surgical assistance system 100 may obtain a pre-morbid model of the bone. The pre-morbid model of the bone may represent a state of the bone prior to an onset of a morbidity of the bone. For example, the pre-morbid model of the bone may represent a state of the bone prior to the onset of a morbidity (e.g., arthritis, trauma, etc.) that led to the initial orthopedic surgery on the bone.

Surgical assistance system 100 may obtain the pre-morbid model of the bone in one of various ways. For example, surgical assistance system 100 may use medical imaging data of the patient generated prior to onset of the morbidity to generate the pre-morbid model of the bone. In another example, surgical assistance system 100 may retrieve a preexisting pre-morbid model of the bone from a data storage system.

In another example, surgical assistance system 100 may generate the pre-morbid model of the bone using mean statistical shape modeling. Prior to using mean statistical shape modeling to reconstruct the pre-morbid model of the bone, measurements of several parameters of a large number of patients may be obtained. In some examples, the param-eters may include demographic parameters, such as age, gender, height, weight, ethnicity, and so on. Furthermore, in some examples, the parameters include anatomic parameters regarding one or more bones. For instance, in an example involving the humerus, the anatomic parameters may include the humeral diaphysis diameter, the humeral surgical neck diameter, humeral head sphere diameter, and so on.

To reconstruct the pre-morbid model of the bone of a current patient undergoing orthopedic revision surgery, sur-gical assistance system 100 may rescale and adjust a mean SSM of the bone to the current patient bone. The mean SSM of the bone is a model of the bone based on average dimensions of the bone. Scaling is a process to make the mean SSM fit the patient bone size. For example, if the bone of the current patient is longer than the mean SSM, surgical assistance system 100 may scale up the mean SSM to have the length of the bone of the current patient. Surgical assistance system 100 may then apply a non-rigid transfor-mation registration process to the rescaled mean SSM to deform a shape of the rescaled mean SSM to fit the patient bone. The bone model points used in the non-rigid trans-formation registration process may include points of a 3D model of the bone of the current patient except for morbid areas of the bone of the current patient, such as an articular surface or an arthritic surface. In other words, surgical assistance system 100 may deform the rescaled mean SSM to have the measurements of the bone of the current patient, except for measurements involving morbid areas.

Furthermore, as part of determining the damaged and intact parts of the bone based on the first intra-revision model, surgical assistance system 100 may register the first intra-revision model of the bone with the pre-morbid model of the bone. Examples of registering the first intra-revision model of the bone with the pre-morbid model of the bone are set forth elsewhere in this disclosure. After registering the first intra-revision model of the bone with the pre-morbid model of the bone, surgical assistance system 100 may compare the first intra-revision model of the bone with the pre-morbid model of the bone to determine which parts of the pre-morbid model of the bone are missing from the first intra-revision model of the bone. Surgical assistance system 100 may classify the parts of the pre-morbid model of the bone that are missing from the first intra-revision model of the bone as damaged parts of the bone. Surgical assistance system 100 may classify the parts of the pre-morbid model of the bone that are not missing from the first intra-revision model of the bone as intact parts of the bone.

In other words, for each region of the pre-morbid model of the bone, surgical assistance system 100 may perform a comparison that compares the region of the pre-morbid model of the bone to a corresponding region of the first intra-revision model of the bone.

Surgical assistance system 100 may also determine, based on the comparison, whether the region contains bone in both the pre-morbid model of the bone and the first intra-revision model of the bone. Surgical assistance system 100 may then perform one of the following for the region: (1) determine that the region is one of the intact parts of the bone based the region containing bone in both the pre-morbid model of the bone and the first intra-revision model of the bone; or (2) determine that the region is one of the damaged parts of the bone based on the region not containing bone in both the pre-morbid model of the bone and the first intra-revision model of the bone.

After determining the damaged and intact parts of the bone, surgical assistance system 100 may generate an intra-revision model (e.g., a second intra-revision model) of the bone at least in part by modifying the pre-revision model of the bone to exclude the damaged parts of the bone. As part of generating the second intra-revision model of the bone, surgical assistance system 100 may register the pre-revision model of the bone with the pre-morbid model of the bone. Surgical assistance system 100 may then morph the pre-revision model of the bone such that the damaged portions of the bone are outside the exterior surface of the pre-revision model of the bone. It is noted that the pre-morbid model of the bone is not modified to generate the second intra-revision model of the bone because the pre-revision model of the bone may be more accurate than the pre-morbid model of the bone and other virtual objects may already be defined in spatial relationships with the pre-revision model of the bone.

In some examples, after generating the second intra-revision model of the bone, surgical assistance system 100 may generate a revised surgical plan for the orthopedic revision surgery based on the second intra-revision model of the bone. For example, surgical assistance system 100 may determine a different implant component to use, determine a different bone graft to use, determine a different position or orientation of an orthopedic prosthesis, determine different fixation elements associated with the orthopedic prosthesis, different cutting planes, different drilling or reaming axes, or otherwise recommend different orthopedic components or actions to perform the orthopedic revision surgery.

In some examples, surgical assistance system 100 may generate registration data that describes a spatial relationship between the second intra-revision model of the bone and the actual bone of the patient. Because the second intra-revision model of the bone has been modified to exclude the damaged parts of the bone, it is more likely that surgical assistance system 100 is able to accurately register the second intra-revision model of the bone and the actual bone of the patient than it would be to register the pre-revision model of the bone with the actual bone of the patient. This is at least in part because, during the registration process, surgical assistance system 100 does not attempt to match landmarks of the pre-revision model of the bone that correspond to damaged parts of the bone with missing parts of the actual bone.

Subsequently, MR visualization device 104 of surgical assistance system 100 may generate, based on the registration data, a MR visualization that includes a virtual object that is defined by the revised surgical plan at a position that has a stable spatial relationship to the bone from a perspective of a user (e.g., user 118) that perceives the MR visualization. The virtual object may provide information to the user about the orthopedic revision surgery. For example, the virtual object may indicate a drilling axis, cutting plane, reaming axis, etc.

The techniques of this disclosure may be applicable to various bones. For example, the techniques of this disclosure may be applicable to a scapula of the patient, a humerus of the patient, a fibula of the patient, a patella of the patient, a tibia of the patient, a talus of the patient, a hip of the patient, a femur of the patient, or another type of bone of the patient.

Figure 2:
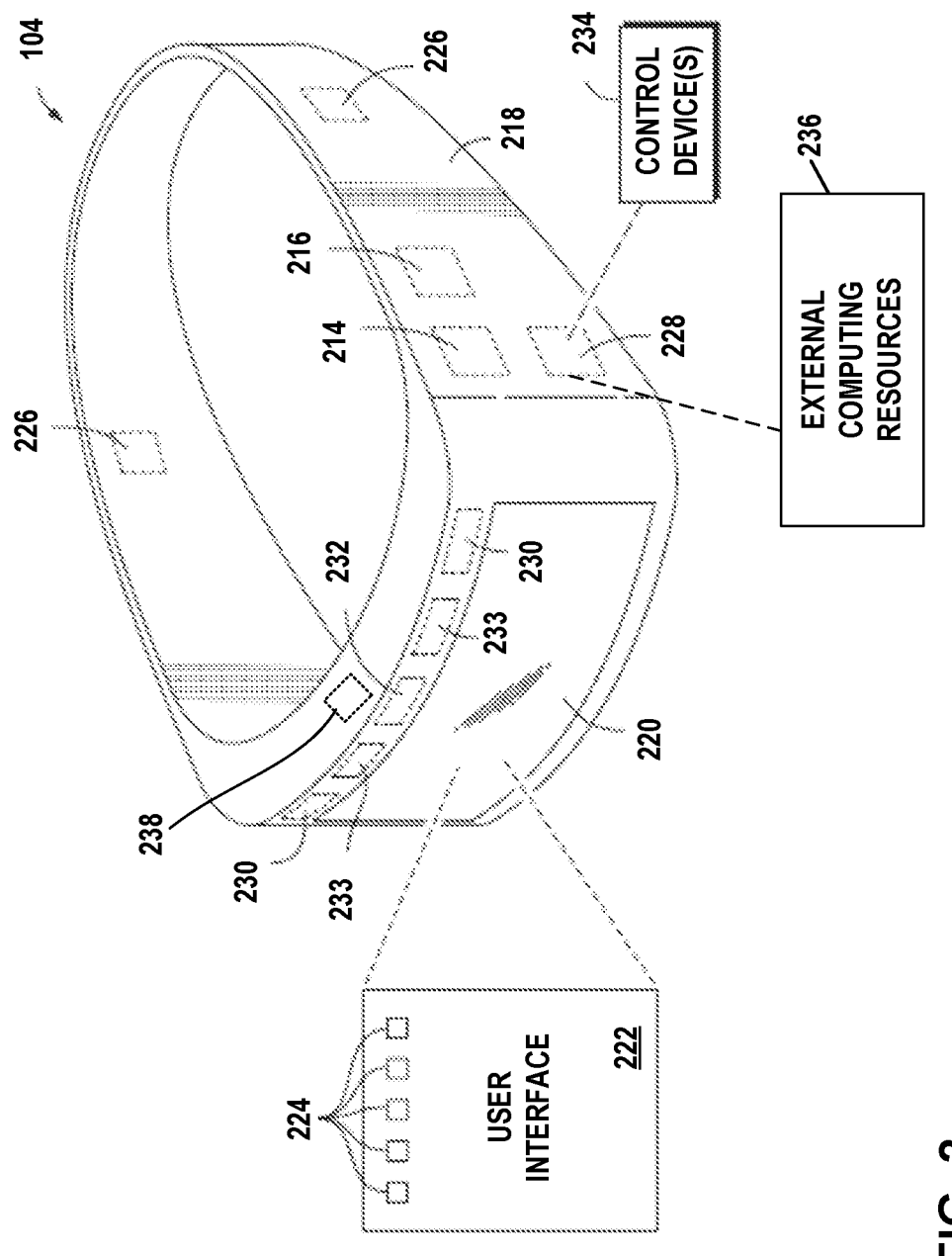
FIG. 2 is a schematic representation of a mixed reality (MR) visualization device for use in an MR system, according to an example of this disclosure.

FIG. 2 is a schematic representation of MR visualization device 104 for use in an MR system, such as MR visualization device 104 of FIG. 1, according to an example of this disclosure. As shown in the example of FIG. 2, MR visualization device 104 can include a variety of electronic components found in a computing system, including one or more processor(s) 214 (e.g., microprocessors or other types of processing units) and memory 216 that may be mounted on or within a frame 218. Furthermore, in the example of FIG. 2, MR visualization device 104 may include a transparent screen 220 that is positioned at eye level when MR visualization device 104 is worn by a user. In some examples, screen 220 can include one or more liquid crystal displays (LCDs) or other types of display screens on which images are perceptible to a surgeon who is wearing or otherwise using MR visualization device 104 via screen 220. Other display examples include organic light emitting diode (OLED) displays. In some examples, MR visualization device 104 can operate to project 3D images onto the user's retinas using techniques known in the art.

In some examples, screen 220 may include see-through holographic lenses, sometimes referred to as waveguides, that permit a user to see real-world objects through (e.g., beyond) the lenses and also see holographic imagery projected into the lenses and onto the user's retinas by displays, such as liquid crystal on silicon (LCoS) display devices, which are sometimes referred to as light engines or projectors, operating as an example of a holographic projection system 238 within MR visualization device 104. In other words, MR visualization device 104 may include one or more see-through holographic lenses to present virtual images to a user. Hence, in some examples, MR visualization device 104 can operate to project 3D images onto the user's retinas via screen 220, e.g., formed by holographic lenses. In this manner, MR visualization device 104 may be configured to present a 3D virtual image to a user within a real-world view observed through screen 220, e.g., such that the virtual image appears to form part of the real-world environment. In some examples, MR visualization device 104 may be a Microsoft HOLOLENS™ headset, available from Microsoft Corporation, of Redmond, Washington, USA, or a similar device, such as, for example, a similar MR visualization device that includes waveguides. The HOLOLENS™ device can be used to present 3D virtual objects via holographic lenses, or waveguides, while permitting a user to view actual objects in a real-world scene, i.e., in a real-world environment, through the holographic lenses.

Although the example of FIG. 2 illustrates MR visualization device 104 as a head-wearable device, MR visualization device 104 may have other forms and form factors. For instance, in some examples, MR visualization device 104 may be a handheld smartphone or tablet.

MR visualization device 104 can also generate a user interface (UI) 222 that is visible to the user, e.g., as holographic imagery projected into see-through holographic lenses as described above. For example, UI 222 can include a variety of selectable widgets 224 that allow the user to interact with a MR system, such as MR system 212 of FIG.

1. Imagery presented by MR visualization device 104 may include, for example, one or more 2D or 3D virtual objects. MR visualization device 104 also can include a speaker or other sensory devices 226 that may be positioned adjacent the user's ears. Sensory devices 226 can convey audible information or other perceptible information (e.g., vibrations) to assist the user of MR visualization device 104.

MR visualization device 104 can also include a transceiver 228 to connect MR visualization device 104 to network 106, a computing cloud, such as via a wired communication protocol or a wireless protocol, e.g., Wi-Fi, Bluetooth, etc. MR visualization device 104 also includes a variety of sensors to collect sensor data, such as one or more optical camera(s) 230 (or other optical sensors) and one or more depth camera(s) 232 (or other depth sensors), mounted to, on or within frame 218. In some examples, optical sensor(s) 230 are operable to scan the geometry of the physical environment in which a user of MR system 212 is located (e.g., an operating room) and collect two-dimensional (2D) optical image data (either monochrome or color). Depth sensor(s) 232 are operable to provide 3D image data, such as by employing time of flight, stereo or other known or future-developed techniques for determining depth and thereby generating image data in three dimensions. Other sensors can include motion sensors 233 (e.g., Inertial Mass Unit (IMU) sensors, accelerometers, etc.) to assist with tracking movement.

MR system 212 processes the sensor data so that geometric, environmental, textural, or other types of landmarks (e.g., corners, edges or other lines, walls, floors, objects) in the user's environment or "scene" can be defined and movements within the scene can be detected. As an example, the various types of sensor data can be combined or fused so that the user of MR visualization device 104 can perceive virtual objects that can be positioned, or fixed and/or moved within the scene. When a virtual object is fixed in the scene, the user can walk around the virtual object, view the virtual object from different perspectives, and manipulate the virtual object within the scene using hand gestures, voice commands, gaze line (or direction) and/or other control inputs. In some examples, the sensor data can be processed so that the user can position a 3D virtual object (e.g., a bone model) on an observed physical object in the scene (e.g., a surface, the patient's real bone, etc.) and/or orient the 3D virtual object with other virtual objects displayed in the scene. In some examples, the sensor data can be processed so that the user can position and fix a virtual representation of the surgical plan (or other widget, image or information) onto a surface, such as a wall of the operating room. Yet further, in some examples, the sensor data can be used to recognize surgical instruments and the position and/or location of those instruments.

MR visualization device 104 may include one or more processors 214 and memory 216, e.g., within frame 218 of the visualization device. In some examples, one or more external computing resources 236 process and store information, such as sensor data, instead of or in addition to in-frame processor(s) 214 and memory 216. For example, external computing resources 236 may include processing circuitry 108, memory 110, and/or other computing resources of computing device 102 (FIG. 1). In this way, data processing and storage may be performed by one or more processors 214 and memory 216 within MR visualization device 104 and/or some of the processing and storage requirements may be offloaded from MR visualization device 104. Hence, in some examples, one or more processors that control the operation of MR visualization device

104 may be within MR visualization device 104, e.g., as processor(s) 214. Alternatively, in some examples, at least one of the processors that controls the operation of MR visualization device 104 may be external to MR visualization device 104, e.g., as processor(s) 210. Likewise, operation of MR visualization device 104 may, in some examples, be controlled in part by a combination of one or more processors 214 within the visualization device and one or more processors 210 external to MR visualization device 104.

For instance, in some examples, when MR visualization device 104 is in the context of FIG. 2, processing of the sensor data can be performed by processing device(s) 210 in conjunction with memory or storage device(s) (M) 215. In some examples, processor(s) 214 and memory 216 mounted to frame 218 may provide sufficient computing resources to process the sensor data collected by cameras 230, 232 and motion sensors 233. In some examples, the sensor data can be processed using a Simultaneous Localization and Mapping (SLAM) algorithm, or other algorithms for processing and mapping 2D and 3D image data and tracking the position of MR visualization device 104 in the 3D scene. In some examples, image tracking may be performed using sensor processing and tracking functionality provided by the Microsoft HOLOLENS™ system, e.g., by one or more sensors and processors 214 within a MR visualization device 104 substantially conforming to the Microsoft HOLOLENS™ device or a similar mixed reality (MR) visualization device.

In some examples, MR system 212 can also include user-operated control device(s) 234 that allow the user to operate MR system 212, use MR system 212 in spectator mode (either as master or observer), interact with UI 222 and/or otherwise provide commands or requests to processing device(s) 210 or other systems connected to network 208. As examples, control device(s) 234 can include a microphone, a touch pad, a control panel, a motion sensor or other types of control input devices with which the user can interact.

FIG. 3 is a flowchart illustrating an example operation of surgical assistance system 100, in accordance with one or more techniques of this disclosure. The flowcharts of this disclosure are provided as examples. Other operations in accordance with the techniques of this disclosure may involve more, fewer, or different actions. For instance, in the example of FIG. 3, one or more of actions (308), (310), or (312) may be omitted.

Figure 4:
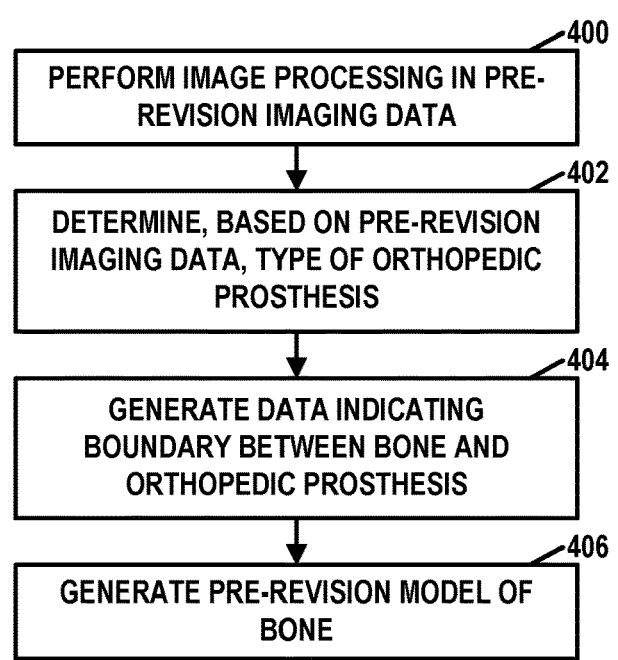
FIG. 4 is a flowchart illustrating an example operation of the surgical assistance system to generate a pre-revision model of a bone, in accordance with one or more techniques of this disclosure.

In the example of FIG. 3, surgical assistance system 100 may obtain a pre-revision model of a bone of a patient (300). The pre-revision model of the bone represents a pre-revision state of the bone after a prior orthopedic surgery on the bone and before the orthopedic revision surgery. It is assumed in FIG. 3 that an orthopedic prosthesis was attached to the bone during the prior orthopedic surgery. Surgical assistance system 100 may obtain the pre-revision model of the bone in one or more of various ways. For instance, surgical assistance system 100 may retrieve or generate the pre-revision model of the bone. FIG. 4 is a flowchart illustrating an example operation to generate the pre-revision model of the bone. In other examples, surgical assistance system 100 does not identify a type of orthopedic prosthesis or generate data indicating a boundary between bone and the orthopedic prosthesis.

Furthermore, in the example of FIG. 3, surgical assistance system 100 may obtain intra-revision imaging data of the bone (302). The intra-revision imaging data of the bone represents an intra-revision state of at least a portion of the bone during the orthopedic revision surgery after removal of the orthopedic prosthesis from the bone. Accordingly, the intra-revision imaging data may show bone loss caused by removal of the orthopedic prosthesis from the bone. The intra-revision imaging data may include imaging data from MR visualization device 104 or another device. Example types of intra-revision imaging data may include 3D image data, such as stereoscopic RGB data, data from a depth camera of MR visualization device 104, or other types of imaging data.

Figure 5:
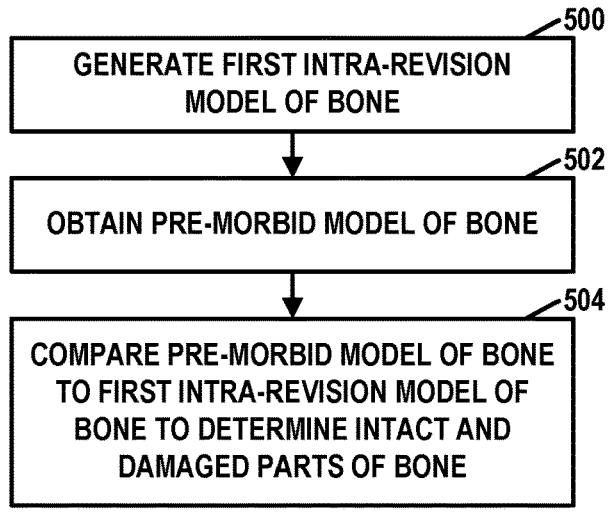
FIG. 5 is a flowchart illustrating an example operation of the surgical assistance system for determining damaged and intact parts of a bone, in accordance with one or more techniques of this disclosure.

Surgical assistance system 100 may determine, based on the intra-revision imaging data, damaged and intact parts of the bone (304). Surgical assistance system 100 may determine the damaged and intact parts of the bone in various ways. For instance, in one example, surgical assistance system 100 may compare imaging data of the bone from an earlier orthopedic surgery involving the bone to the intra-revision imaging data and determine differences. In some examples, surgical assistance system 100 may generate a first intra-revision model of the bone based on the intra-revision imaging data. The first intra-revision model of the bone represents an intra-revision state of at least the portion of the bone during the orthopedic revision surgery after removal of the orthopedic prosthesis from the bone. The first intra-revision model of the bone may comprise a point cloud of 3-dimensional locations. FIG. 5, which is described in detail below, is a flowchart illustrating an example operation to determine damaged and intact parts of the bone based on the first intra-revision model of the bone. In other examples, surgical assistance system 100 may use operations other than that shown in FIG. 5 to determine the damaged and intact parts of the bone.

Next, surgical assistance system 100 may generate an intra-revision model of the bone by modifying the pre-revision model of the bone to exclude damaged parts of the bone (306). To differentiate this intra-revision model of the bone from the intra-revision model of the bone generated in some examples based on the intra-revision imaging data, this disclosure may refer to the intra-revision model of the bone generated by modifying the pre-revision model as the "second intra-revision model of the bone."

In one example, to modify the pre-revision model, surgical assistance system 100 may represent the pre-revision model as a set of 3-dimensional blocks. In this example, surgical assistance system 100 may evaluate blocks on a surface of the pre-revision model. If the block is not part of an intact part of the bone, surgical assistance system 100 may remove the block. Surgical assistance system 100 may continue to evaluate blocks until there are no more blocks to remove.

Figure 8:
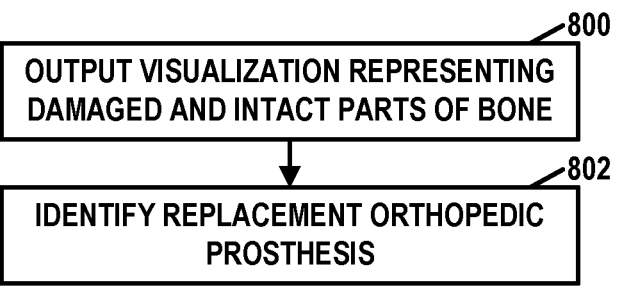
FIG. 8 is a flowchart illustrating an example operation of the surgical assistance system to generate a revised surgical plan based on an intra-revision model of a bone, in accordance with one or more techniques of this disclosure.

In the example of FIG. 3, surgical assistance system 100 may generate a revised surgical plan for the orthopedic revision surgery based on the second intra-revision model of the bone (308). For instance, the revised surgical plan may describe a different orthopedic prosthesis than an orthopedic prosthesis described in an initial surgical plan for the orthopedic revision surgery, different attachment points for the orthopedic prosthesis, or other types of changes from the initial surgical plan for the orthopedic revision surgery. In some examples, the revised surgical plan may indicate that specific cuts are to be performed at specific angles or positions. In some examples, the revised surgical plan may indicate that a drill bit is to enter a bone with a specific trajectory and/or attain a specific drilling depth. Surgical assistance system 100 may generate the revised surgical plan in any one of various ways. FIG. 8, which is described in detail elsewhere in this disclosure, describes an example operation for generating the revised surgical plan.

Furthermore, in the example of FIG. 3, surgical assistance system 100 may generate registration data that describes a spatial relationship between the second intra-revision model of the bone and the actual bone of the patient (310). Surgical assistance system 100 may generate the registration data in various ways. FIG. 7 is an example operation for generating the registration data that describes the spatial relationship between the second intra-revision model of the bone and the actual bone of the patient.

Surgical assistance system 100 may generate an MR visualization that includes a virtual object defined by the revised surgical plan at a position that has a stable spatial relationship to the bone from a perspective of a user (e.g., user 118) that perceives the MR visualization (312). The virtual object provides information to the user about the orthopedic revision surgery. For example, the virtual bone may represent a drilling axis, a cutting plane, or another type of surgical guidance. In this example, the drilling axis, cutting plane, etc. may have positions that are defined in fixed relation to the second intra-revision model of the bone. Thus, even if the MR visualization does not include the second intra-revision model of the bone, registering the second intra-revision model of the bone with the actual bone of the patient may enable surgical assistance system 100 to present the virtual objects at correct positions relative to the actual bone of the patient.

In some examples, as an alternative, or in addition, to surgical assistance system 100 generating an MR visualization, surgical assistance system 100 may provide instructions to a surgical robot to perform specific surgical tasks according to the revised surgical plan. For example, the robot may include a robotic arm having attached thereto a drill or cutting burr. The robot may use the drill to create holes or insert pins into a bone of the patient. The robot may use the cutting burr to remove sections of a bone, such as a humeral head. The robot may be able to drill and cut with greater precision than a human surgeon may be able to achieve. Surgical assistance system 100 may configure the robot to drill or cut at positions and along trajectories or planes indicated by the revised surgical plan.

FIG. 4 is a flowchart illustrating an example operation of surgical assistance system 100 to generate a pre-revision model of a bone, in accordance with one or more techniques of this disclosure. In the example of FIG. 4, surgical assistance system 100 may perform image processing on pre-revision imaging data (400). For instance, in examples where the pre-revision imaging data includes CT images, surgical assistance system 100 may apply one or more digital filters to the CT images to reduce black and white bands that may appear in the CT images. In some examples where the pre-revision imaging data includes CT images, surgical assistance system 100 may apply one or more digital filters to remove outlier samples (e.g., samples having values that are beyond x standard deviations from a mean of the sample values). In some examples, surgical assistance system 100 may up-sample, down-sample, or crop the CT images.

Furthermore, in the example of FIG. 4, surgical assistance system 100 may determine, based on the pre-revision imaging data, a type of orthopedic prosthesis that is attached to the bone (402). For instance, in an example where a total shoulder arthroplasty was previously performed on a patient, surgical assistance system 100 may determine, based on the pre-revision imaging data, whether the total shoulder arthroplasty was an anatomic total shoulder arthroplasty (i.e., a total shoulder arthroplasty in which a cup-shaped prosthesis is attached to the patient's scapula and a ball-shaped prosthesis is attached to the patient's humerus) or a reverse total shoulder arthroplasty (i.e., a total shoulder arthroplasty in which a ball-shaped prosthesis is attached to the patient's scapula and a cup-shaped prosthesis is attached to the patient's humerus). In some examples, surgical assistance system 100 may distinguish among different sub-types of the same type of orthopedic prosthesis. For instance, in one example, surgical assistance system 100 may distinguish between stemmed and stemless humeral implants. In some examples, surgical assistance system 100 may distinguish among different sizes of a type of orthopedic prosthesis. For instance, surgical assistance system 100 may distinguish among humeral implants having stems of different lengths.

Surgical assistance system 100 may apply an AI-based image recognition system to determine the type of orthopedic prosthesis. For example, surgical assistance system 100 may use a convolutional neural network that has previously been trained to identify types of orthopedic prostheses from imaging data. In this example, the pre-revision imaging data may include one or more 2-dimensional radiographs and surgical assistance system 100 may provide the 2-dimensional radiographs as input to the convolutional neural network.

Additionally, in the example of FIG. 4, surgical assistance system 100 may generate, based on the pre-revision imaging data, data indicating a boundary between the orthopedic prosthesis and the bone (404). In other words, surgical assistance system 100 may determine which parts of a body that includes the bone and the orthopedic prosthesis are the bone and which parts of the body are the orthopedic prosthesis.

Surgical assistance system 100 may use an AI-based system to determine the boundary between the orthopedic prosthesis and the bone. In some examples, the AI-based system may use the previously determined type of the orthopedic prosthesis as input. In other examples, actions 402 and 404 are reversed and surgical assistance system 100 may use the data indicating the boundary between the orthopedic prosthesis and the bone as input to the AI-based system for determining the type of the orthopedic prosthesis.

Furthermore, surgical assistance system 100 may generate, based on the pre-revision imaging data and the data indicating the boundary between the bone and the orthopedic prosthesis, a pre-revision model of the bone (406). That is, surgical assistance system 100 may generate a 3-dimensional virtual model of the bone as the bone currently exists separate from the orthopedic prosthesis. Thus, in some examples, after generating the pre-revision model of the bone, MR visualization device 104 may present a MR visualization in which user 108 may view the bone in isolation from the orthopedic prosthesis, view the orthopedic prosthesis in isolation from the bone, or view a combination of the orthopedic prosthesis and the bone.

Surgical assistance system 100 may use one of various techniques to generate the pre-revision model of the bone. For instance, in one example, to generate the pre-revision model of the bone, surgical assistance system 100 may generate a 3-dimensional virtual model of a body that includes both the bone and the orthopedic prosthesis based on CT images, in accordance with conventional CT modeling techniques. Additionally, in this example, surgical assistance system 100 may use the data indicating the boundary between the bone and orthopedic prosthesis to mark portions of this 3-dimensional virtual model as belonging to the bone or belonging to the orthopedic prosthesis.

FIG. 5 is a flowchart illustrating an example operation of surgical assistance system 100 for determining damaged and intact parts of a bone, in accordance with one or more techniques of this disclosure. As illustrated in the example of FIG. 5, surgical assistance system 100 may generate a first intra-revision model of at least part of the bone based on intra-revision imaging data (500). The first intra-revision model of the bone may be a 3-dimensional virtual model of an intra-revision state of the bone. The intra-revision state of the bone occurs during the orthopedic revision surgery after removal of an existing orthopedic prosthesis from the bone. In some examples, because the orthopedic revision surgery typically does not expose all of the bone, the intra-revision imaging data may represent only those parts of the bone that are exposed.

Surgical assistance system 100 may generate the first intra-revision model of the bone in any of various ways. For instance, in one example, the intra-revision imaging data may include depth images of the intra-revision state of the bone. The depth images of the bone may be captured from one or more angles. Surgical assistance system 100 may use the depth images to determine a 3-dimensional surface of at least part of the bone. For instance, surgical assistance system 100 may generate point clouds based on the depth images and then perform a registration process to align the point clouds. Surgical assistance system 100 may use points in the resulting aligned point clouds as vertices of the 3-dimensional virtual model of the intra-revision state of the bone. In some examples, surgical assistance system 100 may use intra-revision imaging data from MR visualization device 104 as input to a SLAM algorithm to generate the first intra-revision model of the bone.

Furthermore, in the example of FIG. 5, surgical assistance system 100 may obtain a pre-morbid model of the bone (502). The pre-morbid model of the bone is a 3-dimensional virtual model of the bone as it likely existed prior to onset of a morbidity, such as a morbidity that led to performance of the previous orthopedic surgery. In some examples, surgical assistance system 100 may obtain the pre-morbid model of the bone from a local or remote data storage system. In other examples, surgical assistance system 100 may generate the pre-morbid model of the bone. For instance, in some examples, surgical assistance system 100 may use mean statistical shape modeling (SSM) to generate the pre-morbid model of the bone. In some examples, to use mean statistical shape modeling to generate the pre-morbid model of the bone, surgical assistance system 100 may obtain statistics regarding a shape of the bone from a patient-specific model of the bone. Such statistics may include the version of the bone, the length of the bone, the diameter of the bone at various points in the bone, and so on. Surgical assistance system 100 may compare the statistics with the statistics of reference models in a library of models of the bone to select a reference model from the library of reference models of the bone. For instance, surgical assistance system 100 may determine sums of absolute differences associated with each reference model in the library of models. The sum of absolute differences for a reference model may indicate a sum of differences between corresponding statistics of the reference model and the patient-specific model. Surgical assistance system 100 may select the reference model associated with the smallest sum of absolute differences. In some examples, surgical assistance system 100 use the pre-morbid model of the bone as the patient-specific model of the bone. In other examples, surgical assistance system 100 may use the first intra-revision model of the bone as the patient-specific model of the bone.

Other example techniques for statistical shape modeling are described elsewhere in this disclosure.

Figure 6:
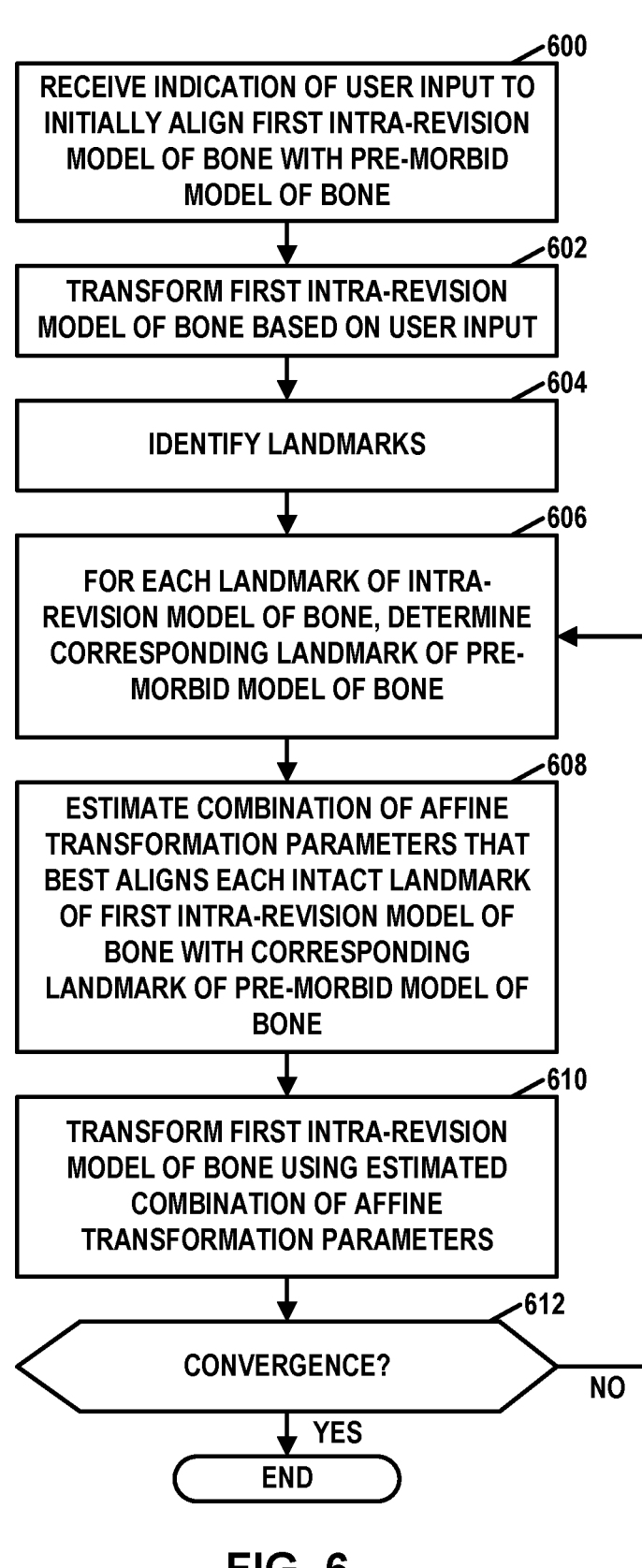
FIG. 6 is a flowchart illustrating an example operation of the surgical assistance system to register a pre-morbid model of the bone and a first intra-revision model of the bone, in accordance with one or more techniques of this disclosure.

Subsequently, surgical assistance system 100 may compare the pre-morbid model of the bone to the first intra-revision model of the bone to determine the intact and damaged parts of the bone (504). For instance, in one example, surgical assistance system 100 may register the pre-morbid model of the bone with the first intra-revision model of the bone, thereby aligning the pre-morbid model of the bone with the first intra-revision model of the bone. FIG. 6, which is described in detail elsewhere in this disclosure, is an example operation to register the pre-morbid model of the bone with the first intra-revision model of the bone. Surgical assistance system 100 may then perform a characterization process for each region of the pre-morbid model of the bone. Each of the regions may be a 3-dimensional volume (e.g., 1 cubic millimeter). When performing the characterization process for a region, surgical assistance system 100 may determine whether the region is part of the bone in both the pre-morbid model of the bone and the first intra-revision model of the bone. If the region is part of the bone in both the pre-morbid model of the bone and the first intra-revision model of the bone, surgical assistance system 100 marks the region as an intact part of the bone. Otherwise, if the region is part of the bone in only one of the pre-morbid model of the bone and the first intra-revision model of the bone, surgical assistance system 100 marks the region as a damaged part of the bone.

FIG. 6 is a flowchart illustrating an example operation of surgical assistance system 100 to register a pre-morbid model of the bone and the first intra-revision model of the bone, in accordance with one or more techniques of this disclosure. In the example of FIG. 6, surgical assistance system 100 may receive an indication of user input to initially align the first intra-revision model of the bone with the pre-morbid model of the bone (600). For instance, in one example, MR visualization device 104 may present a MR visualization containing both the pre-morbid model of the bone and the intra-revision model of the bone. In this example, MR visualization device 104 may receive indications of user input, such as hand gestures or eye gestures, that move either or both of the pre-morbid or first intra-revision models of the bone to be in general alignment in 3-dimensional space. This initial alignment of the pre-morbid model of the bone and the first intra-revision model of the bone may improve the accuracy of the registration process. In other examples, surgical assistance system 100 performs the initial alignment process without receiving indications of user input. In some examples, the user input to align the pre-morbid model of the bone and the first intra-revision model of the bone includes user input to rotate, translate, and/or scale either or both of the pre-morbid model of the bone and the first intra-revision model of the bone.

Surgical assistance system 100 may transform the first intra-revision model of the bone based on the user input (602). For instance, surgical assistance system 100 may modify coordinates of points of the intra-revision model of the bone based on the user input. In other examples, surgical assistance system 100 may transform the pre-morbid model of the bone based on the user input.

Furthermore, surgical assistance system 100 may identify a set of landmarks in the pre-morbid model of the bone and the intra-revision model of the bone that are unlikely to be affected by the morbidity or the removal of the existing orthopedic implant (604). For instance, in an example where the bone is a patient's scapula, surgical assistance system

100 may identify landmarks in the models corresponding to the tip of the patient's acromion, the patient's coracoid process, the patient's scapular neck, points on an anterior surface of the scapula, and so on. Because these landmarks have a stable position relative to one another and may be visible during the orthopedic revision surgery, the relative positions of the landmarks may be compared in the registration process of the pre-morbid model of the bone and the first intra-revision model of the bone.

Furthermore, in the example of FIG. 6, for each landmark of the intra-revision model of the bone, surgical assistance system 100 may determine a corresponding landmark of the pre-morbid model of the bone (606). The landmarks may be points defining the models of the bone or a subset thereof. In some examples, surgical assistance system 100 may determine that the corresponding landmark of the pre-morbid model of the bone is the spatially closest landmark of the pre-morbid model to the landmark of the first intra-revision model. In another example, surgical assistance system 100 may determine a topographical prominence value for each of the landmarks in the pre-morbid and first intra-revision models of the bone. In this example, surgical assistance system 100 may determine that the corresponding landmark in the pre-morbid model of the bone is a landmark that is within a given radius that has a similar topographical prominence as the landmark of the first intra-revision model of the bone.

Surgical assistance system 100 may then estimate a combination of affine transformation parameters that best aligns each of the intact bone landmarks with the corresponding landmark of pre-morbid model of the bone (608). For instance, surgical assistance system 100 may use a root mean square point-to-point distance metric minimization technique to align the corresponding landmarks.

Next, surgical assistance system 100 may transform the first intra-revision model of the bone using the estimated combination of affine transformation parameters (610). For example, surgical assistance system 100 may use a transform defined by the estimated combination of affine transformation parameters to determine updated coordinates of the landmarks in the first intra-revision model of the bone.

Surgical assistance system 100 may then determine whether convergence has occurred (612). Convergence may occur when surgical assistance system 100 determines that differences in position and scale between a previous iteration and the current iteration are below a predetermined threshold. In some examples, surgical assistance system 100 may determine that convergence has occurred after a given number of iterations. Based on determining that convergence has not occurred ("NO" branch of 612), surgical assistance system 100 may repeat actions 606-612 using the transformed first intra-revision model of the bone. However, based on determining that convergence has occurred ("YES" branch of 612), surgical assistance system 100 may end the registration process.

FIG. 7 is a flowchart illustrating an example operation of surgical assistance system 100 to register an intra-revision model of the bone with the actual, real-world bone of a patient, in accordance with one or more techniques of this disclosure. In the example of FIG. 7, the intra-revision model of the bone may be the second intra-revision model of the bone (i.e., the version of the pre-revision model of the bone transformed to exclude damaged portions of the bone). In the example of FIG. 7, surgical assistance system 100 may use a SLAM algorithm to generate a point cloud that includes points on the actual bone of the patient (700). Furthermore, surgical assistance system 100 may receive an indication of user input to initially align the intra-revision model of the bone with the actual bone (702). For instance, in one example, MR visualization device 104 of surgical assistance system 100 may output a MR visualization that includes the intra-revision model of the bone. In this example, MR visualization device 104 may receive indications of user input from user 108 to align the intra-revision model of the bone with the actual bone as seen by user 108. Surgical assistance system 100 may then transform the intra-revision model of the bone based on the user input (704). Surgical assistance system 100 may transform the intra-revision model in the same manner as described with respect to action 602 (FIG. 6).

Furthermore, in the example of FIG. 7, surgical assistance system 100 may, for each intact bone landmark of the intra-revision model of the bone, determine a corresponding point in the point cloud of the actual bone (706). Surgical assistance system 100 may determine the corresponding point in the same manner as described with respect to action 606 (FIG. 6). Surgical assistance system 100 may estimate a combination of affine transformation parameters that best aligns each intact bone landmark of the intra-revision model of the bone with corresponding points in the point cloud of the actual bone (708). Surgical assistance system 100 may estimate the combination of affine transformation parameters in the same manner as described with respect to action 608 (FIG. 6). Furthermore, in the example of FIG. 7, surgical assistance system 100 may transform the intra-revision model of the bone using the estimated combination of rotation and translation parameters (710). Surgical assistance system 100 may transform the intra-revision model of the bone in the same manner as described with respect to action 610 (FIG. 6). Surgical assistance system 100 may then determine whether convergence has occurred (712). Surgical assistance system 100 may determine whether convergence has occurred in the same manner as described with respect to action 612 (FIG. 6). Based on a determination that convergence has not yet occurred ("NO" branch of 712), surgical assistance system 100 may repeat actions 706 through 712. Based on a determination that convergence has occurred ("YES" branch of 712), the registration process may end.

FIG. 8 is a flowchart illustrating an example operation of surgical assistance system 100 to generate a revised surgical plan based on an intra-revision model of a bone, in accordance with one or more techniques of this disclosure. In the example of FIG. 8, surgical assistance system 100 may output a visualization representing the damaged and intact parts of the bone (800). For example, MR visualization device 104 of surgical assistance system 100 may output a MR visualization for display to user 118. In this example, the MR visualization may include a virtual model of the bone showing the damaged and intact parts of the bone. In some examples, display 112 of computing device 102 of surgical assistance system 100 may output a visualization representing the damaged and intact parts of the bone.

Viewing the damaged and intact parts of the bone may help user 118 revise the surgical plan for the orthopedic revision surgery. For example, surgical assistance system 100 may receive indications of user input to switch orthopedic prostheses, change the lateralization or medicalization of the orthopedic prosthesis, change the angulation of the orthopedic prosthesis, and so on.

Furthermore, in the example of FIG. 8, surgical assistance system 100 may automatically identify a replacement orthopedic prosthesis suitable for attaching to intact attachment points on the bone (802). Attachment points are points on the bone where screws, nails, or other fastening devices may be used to attach an orthopedic prosthesis to the bone. Because the removal of the previous orthopedic prosthesis may have caused bone loss, the originally planned replacement orthopedic prosthesis may not be suitable for attaching to the attachment points indicated by the original plan for the orthopedic revision surgery. For instance, an arrangement of screw holes in the originally planned replacement orthopedic prosthesis may require one or more of the screws to attach to a part of the bone that is no longer present. Accordingly, surgical assistance system 100 may review of set of pre-made orthopedic prostheses for an orthopedic prosthesis that is suitable for attaching to intact attachment points on the bone. For instance, different ones of the pre-made orthopedic prostheses may have different arrangements of screw holes and surgical assistance system 100 may select one of the pre-made orthopedic prostheses that has a correct arrangement of screw holes to attach to the intact attachment points on the bone.

Figure 9A:
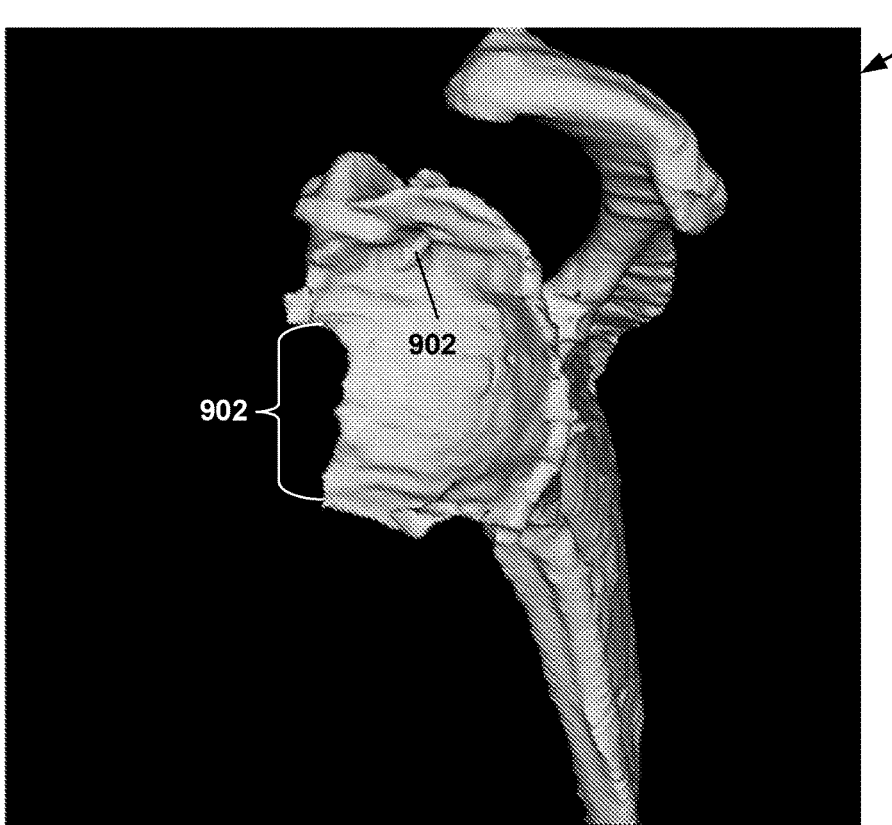
FIG. 9A and FIG. 9B are illustrations of an example intra-revision model of a scapula, in accordance with one or more techniques of this disclosure.
Figure 9B:
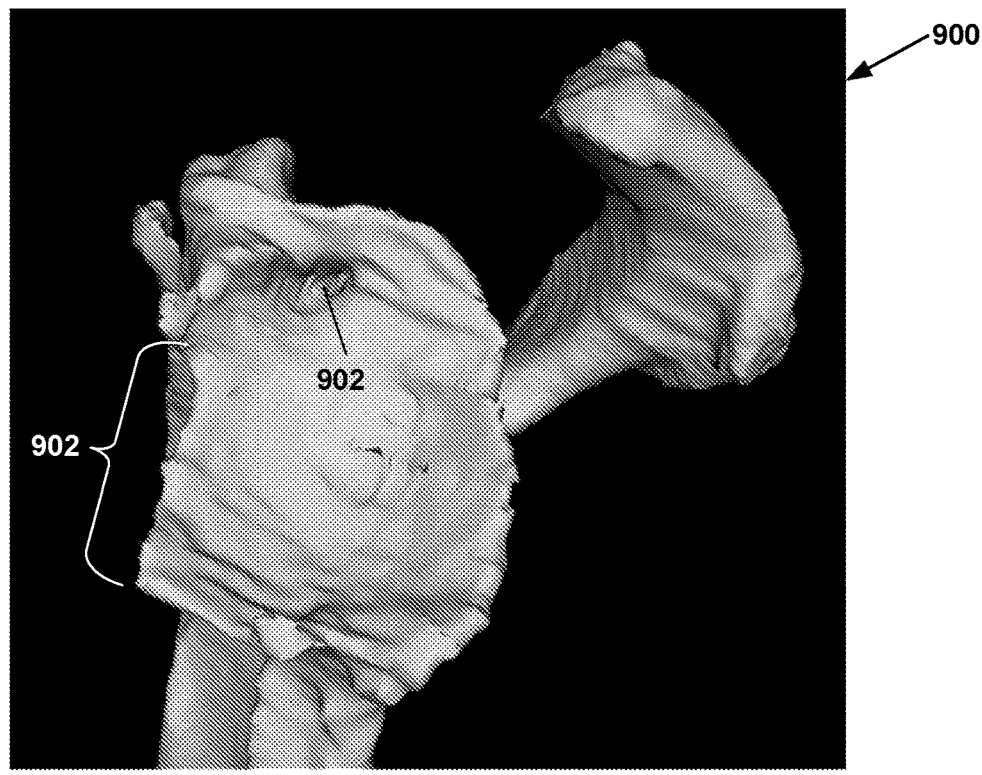
Figure 10A:
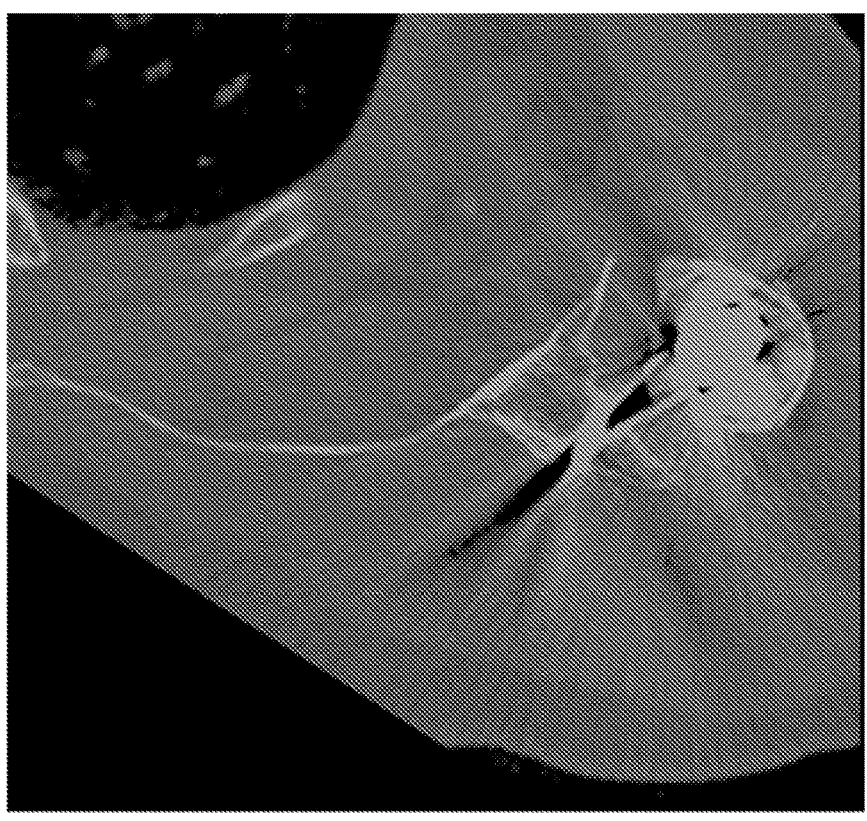
FIG. 10A and FIG. 10B are x-ray images corresponding to the scapula of FIG. 9A and FIG. 9B.
Figure 10B:
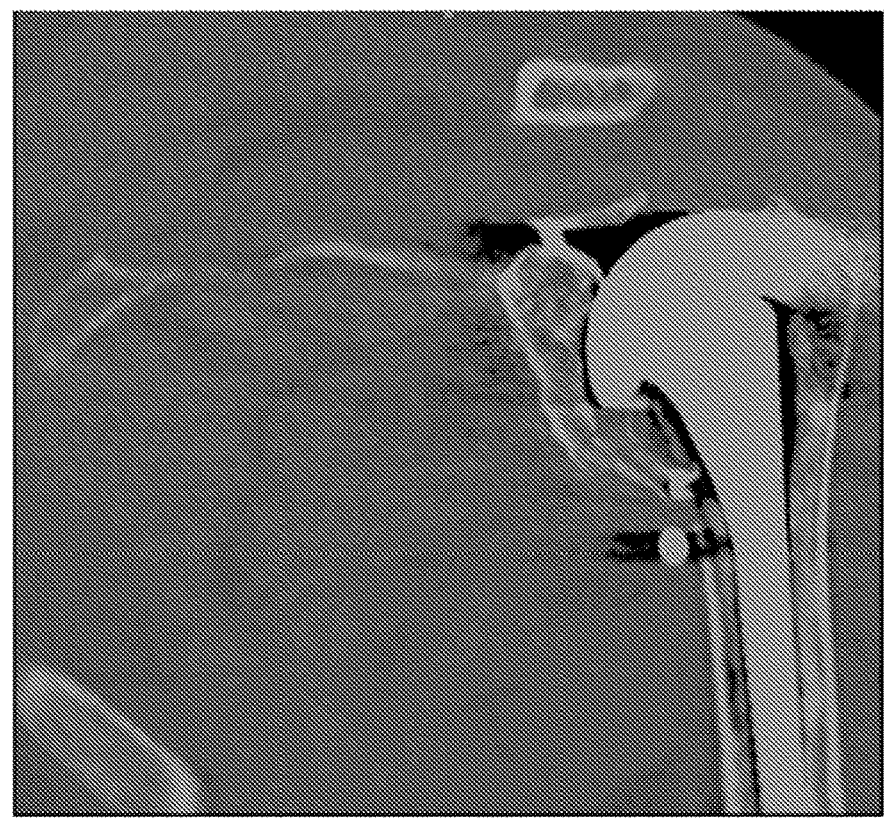

FIG. 9A and FIG. 9B are illustrations of an example intra-revision model of a scapula 900, in accordance with one or more techniques of this disclosure. The intra revision model of scapula 900 is rotated in FIG. 9B relative to FIG. 9A. In the example of FIG. 9A and FIG. 9B, areas 902 are damaged parts of scapula 900. Other parts of scapula 900 are undamaged. FIG. 10A and FIG. 10B are x-ray images corresponding to the scapula of FIG. 9A and FIG. 9B.

Figure 11:
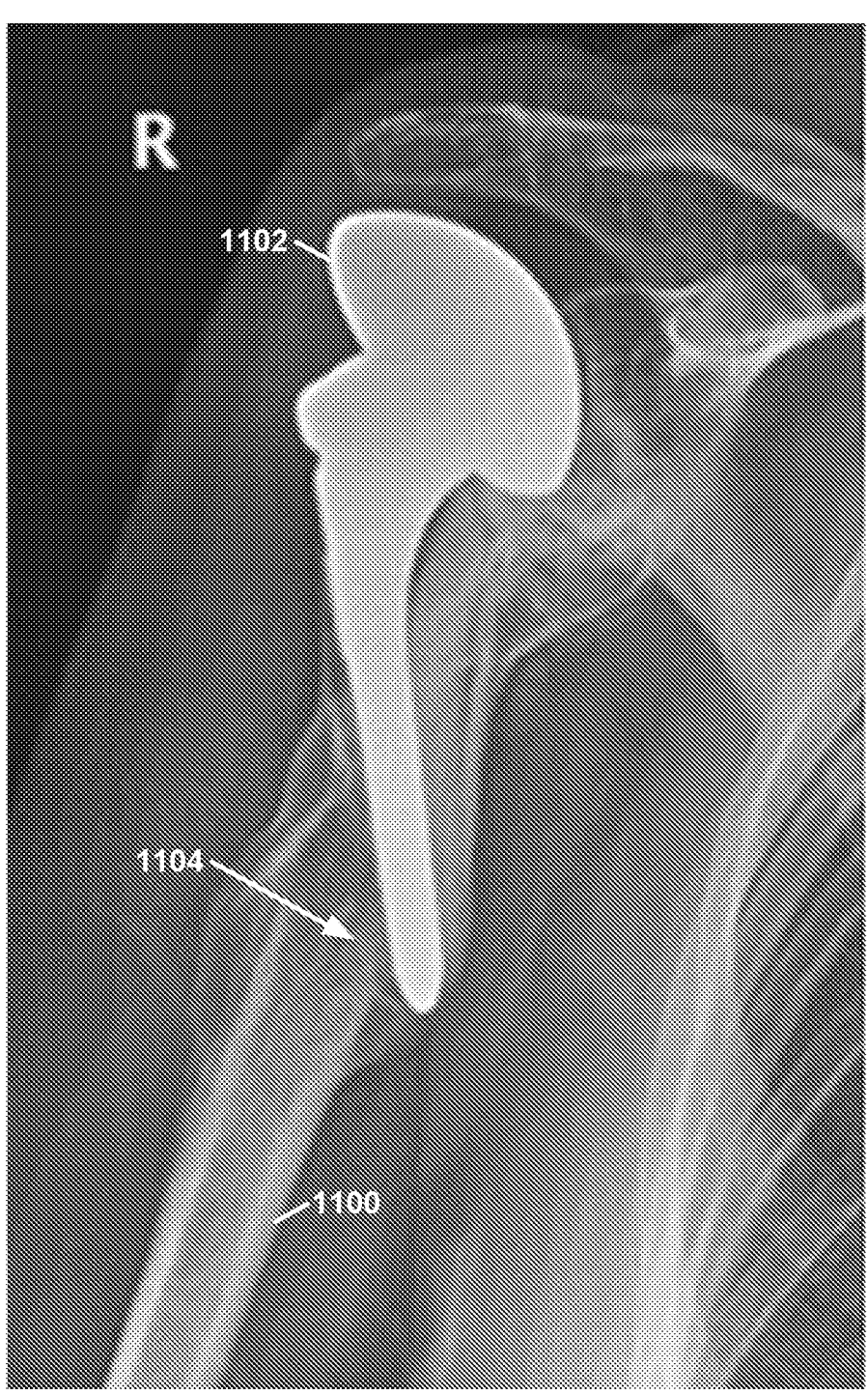
FIG. 11 is an example pre-revision x-ray image of a humerus.
Figure 12:
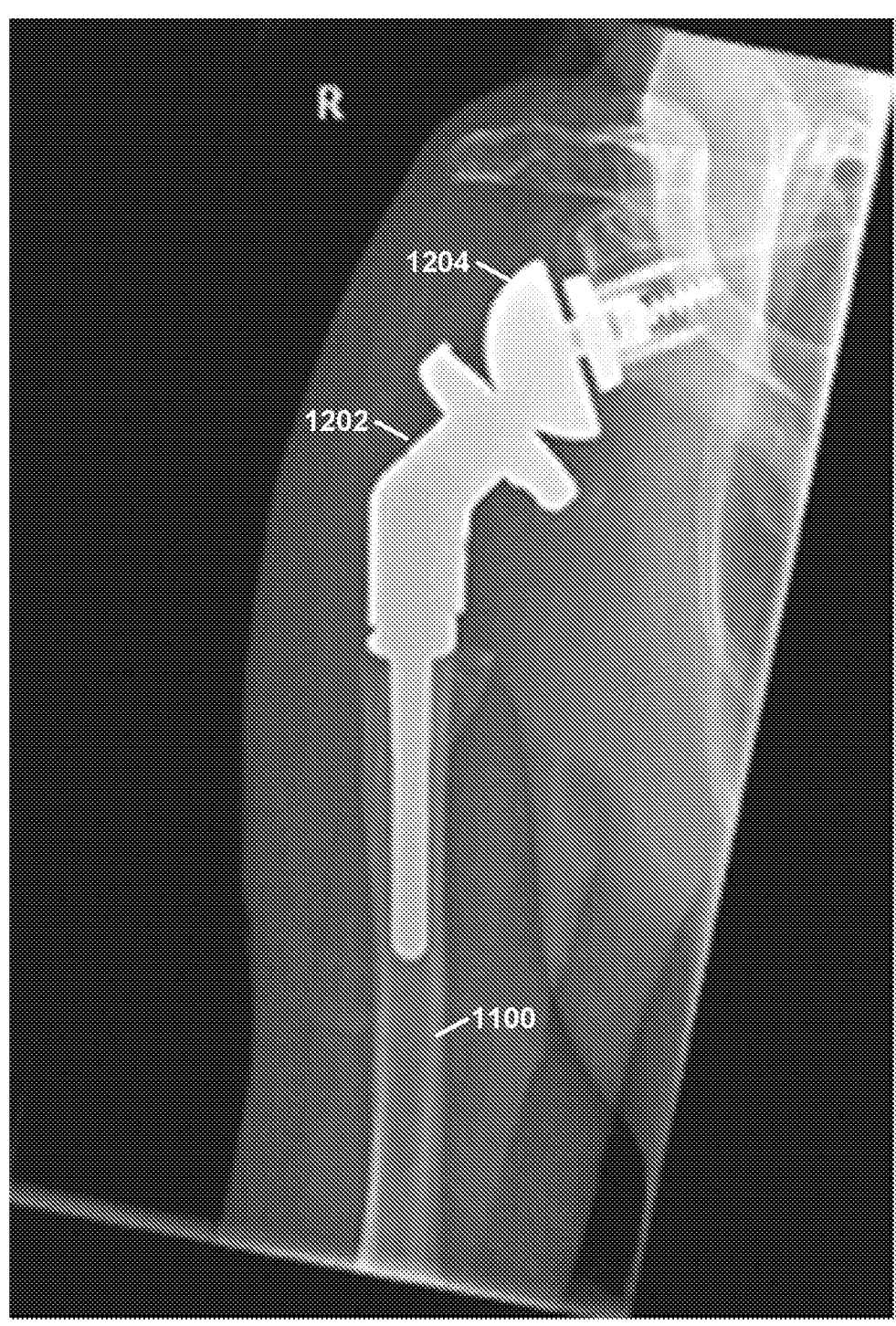
FIG. 12 is an example post-revision x-ray image of the humerus of FIG. 11.

FIG. 11 is an example pre-revision x-ray image of a humerus 1100. As shown in the example of FIG. 11, a stemmed humeral prosthesis 1102 was implanted into humerus 1100, but a fracture has occurred in humerus 1100 near the distal tip of the stemmed humeral prosthesis 1102. FIG. 12 is an example post-revision x-ray image of the humerus 1100 of FIG. 11. As shown in the example of FIG. 12, stemmed humeral prosthesis 1102 (FIG. 11) has been replaced with a different stemmed humeral prosthesis 1202 and a glenoid prosthesis 1204.

Figure 13:
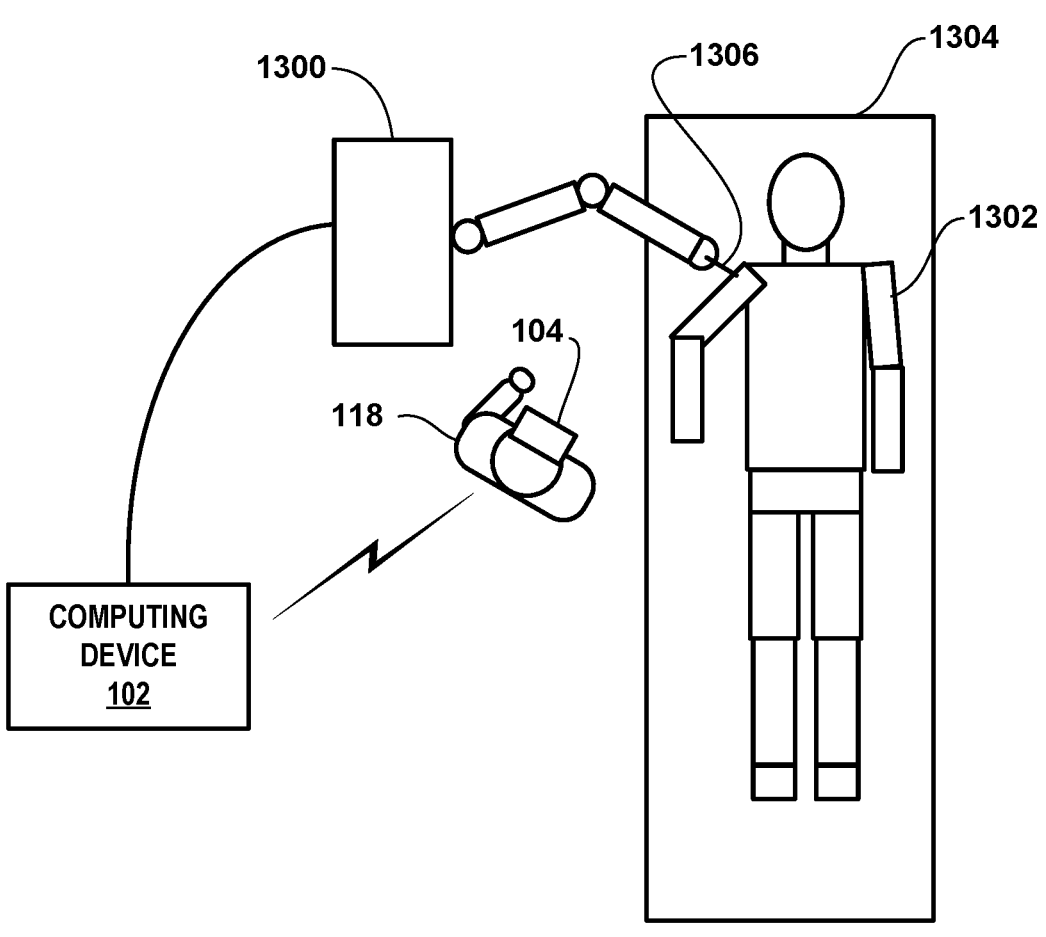
FIG. 13 is a conceptual diagram illustrating an example operating room arrangement that includes a robot, in accordance with one or more techniques of this disclosure.

FIG. 13 is a conceptual diagram illustrating an example operating room arrangement that includes a robot 1300, in accordance with one or more techniques of this disclosure. In the example of FIG. 13, a patient 1302 is lying on a table 1304 undergoing an orthopedic surgery (e.g., a shoulder surgery). User 118 wears MR visualization device 104. Robot 1300 holds a tool 1306, such as a drill or cutting burr. An example of robot 1300 is the Stryker Mako robotic arm interactive orthopedic system. Computing device 102 may be in communication with MR visualization device 104 and robot 1300 and/or MR visualization device 104 and robot 1300 may communicate directly with one another.

Surgical assistance system 100 (e.g., computing device 102 and/or MR visualization device 104) may obtain a pre-revision model of a bone of a patient, e.g., as described above with respect to action 300 of FIG. 3. Additionally, surgical assistance system 100 may obtain intra-revision imaging data of a bone of patient 1302, e.g., as described above with respect to action 302 of FIG. 3. The intra-revision imaging data of the bone represents an intra-revision state of at least a portion of the bone during the orthopedic revision surgery after removal of the orthopedic prosthesis from the bone. Accordingly, the intra-revision imaging data may show bone loss caused by removal of the orthopedic prosthesis from the bone. The intra-revision imaging data may include imaging data obtained from one or more sensors of MR visualization device 104 or another device.

Furthermore, surgical assistance system 100 may determine, based on the intra-revision imaging data, damaged and intact parts of the bone, e.g., as described above with respect to action 304 of FIG. 3. Surgical assistance system 100 may generate an intra-revision model of the bone by modifying the pre-revision model of the bone to exclude damaged parts of the bone, e.g., as described above with respect to action 306 of FIG. 3.

Surgical assistance system 100 may generate a revised surgical plan for the orthopedic revision surgery based on the second intra-revision model of the bone. The revised surgical plan may indicate that specific cuts are to be performed at specific angles or positions. In some examples, the revised surgical plan may indicate that a drill bit is to enter a bone with a specific trajectory and/or attain a specific depth.

Surgical assistance system 100 may determine the revised surgical plan based on the second intra-revision model of the bone in various ways. For instance, in one example, surgical assistance system 100 may determine that a screw needs to pass through a specific amount of bone. Removal of some bone may result in there being less than the specific amount of bone at a planned entry angle for the screw. Accordingly, surgical assistance system 100 may perform a process that uses the second intra-revision model to search for trajectories that enable the screw to pass through the specific amount of bone from the same entry point. In an example where a first humeral implant is being removed and a second humeral implant is being added, removal of the first implant may remove an irregular portion of the proximal end of humerus. In this example, surgical assistance system 100 may use the second intra-revision model to determine a most-proximal plane through the humerus that results in a flat surface that is compatible with a humeral implant in a set of available humeral implants.

After determining the revised surgical plan, surgical assistance system 100 may configure robot 1300 to perform a surgical task based on the revised surgical plan for the orthopedic revision surgery. For example, the revised surgical plan may express positioning parameters for a surgical task (e.g., angles, positions, entry points, depths, etc.) to be performed by robot 1300 relative to the second intra-revision model. Accordingly, in this example, surgical assistance system 100 may share registration data with robot 1300 that maps the second intra-revision model to the actual patient anatomy. Thus, robot 1300 may be able to determine a physical position of tool 1306 held by robot 1300 relative to patient 1302. Robot 1300 may then perform the surgical task according to the positioning parameters. For instance, robot 1300 may drill a hole in a bone of patient 1302 according to an angle indicated by the revised surgical plan.

The following is a non-limiting list of aspects that are in accordance with one or more techniques of this disclosure.

Aspect 1: A computer-implemented method for assisting an orthopedic revision surgery includes obtaining a pre-revision model of a bone of a patient, the pre-revision model of the bone representing a pre-revision state of the bone after a prior orthopedic surgery on the bone and before the orthopedic revision surgery, wherein an orthopedic prosthesis was attached to the bone during the prior orthopedic surgery; obtaining intra-revision imaging data of the bone, the intra-revision imaging data representing an intra-revision state of the bone during the orthopedic revision surgery after removal of the orthopedic prosthesis from the bone; determining, based on the intra-revision imaging data, damaged and intact parts of the bone; and generating a second intra-revision model of the bone by modifying the pre-revision model of the bone to exclude damaged parts of the bone.

Aspect 2: The method of aspect 1, further comprising generating a revised surgical plan for the orthopedic revision surgery based on the second intra-revision model of the bone.

Aspect 3: The method of any of aspects 1-2, the method further comprises: generating registration data that describes a spatial relationship between the intra-revision model of the bone and the bone; and generating, based on the registration data, a MR visualization that includes a virtual object defined by the revised surgical plan at a position that has a stable spatial relationship to the bone from a perspective of a user that perceives the MR visualization, wherein the virtual object provides information to the user about the orthopedic revision surgery.

Aspect 4: The method of any of aspects 1-3, wherein the intra-revision model of the bone is a second intra revision model of the bone and determining the damaged and intact parts of the bone comprises: generating, based on the intra-revision imaging data, a first intra-revision model of the bone, wherein the first intra-revision model of the bone represents the intra-revision state of the bone during the orthopedic revision surgery after removal of the orthopedic prosthesis from the bone; and determining the damaged and intact parts of the bone based on the first intra-revision model of the bone.

Aspect 5: The method of aspect 4, wherein determining the damaged and intact parts of the bone comprises: obtaining a pre-morbid model of the bone; and for each region of the pre-morbid model of the bone: performing a comparison that compares the region of the pre-morbid model of the bone to a corresponding region of the first intra-revision model of the bone; determining, based on the comparison, whether the region contains bone in both the pre-morbid model of the bone and the first intra-revision model of the bone; and one of: determining that the region is one of the intact parts of the bone based the region containing bone in both the pre-morbid model of the bone and the first intra-revision model of the bone; or determining that the region is one of the damaged parts of the bone based on the region not containing bone in both the pre-morbid model of the bone and the first intra-revision model of the bone.

Aspect 6: The method of aspect 5, wherein obtaining the pre-morbid model of the bone comprises using Mean Statistical Shape (MSS) modeling to generate the pre-morbid model of the bone.

Aspect 7: The method of any of aspects 1-6, wherein: the method further comprises: obtaining pre-revision imaging data of the bone, the pre-revision imaging data of the bone representing the pre-revision state of the bone; and generating, based on the pre-revision imaging data of the bone, data indicating a boundary between the orthopedic prosthesis and the bone, and determining the pre-revision model of the bone comprises generating, based on the pre-revision imaging data and the data indicating the boundary of between the orthopedic prosthesis and the bone, the pre-revision model of the bone.

Aspect 8: The method of any of aspects 1-7, wherein the bone is one of: a scapula of the patient, a humerus of the patient, a fibula of the patient, a patella of the patient, a tibia of the patient, a talus of the patient, a hip of the patient, or a femur of the patient.

Aspect 9: The method of any of aspects 2-8, further comprising configuring a robot to perform a surgical task based on the revised surgical plan for the orthopedic revision surgery.

Aspect 10: A computing system for assisting an orthopedic revision surgery includes a storage system configured to store a pre-revision model of the bone, the pre-revision model of the bone representing a pre-revision state of the bone after a prior orthopedic surgery on the bone and before the orthopedic revision surgery, wherein an orthopedic prosthesis was attached to the bone during the prior orthopedic surgery; and one or more processing circuits configured to: obtain intra-revision imaging data of the bone, the intra-revision imaging data representing an intra-revision state of the bone during the orthopedic revision surgery after removal of the orthopedic prosthesis from the bone; determine, based on the intra-revision imaging data, damaged and intact parts of the bone; and generate a second intra-revision model of the bone by modifying the pre-revision model of the bone to exclude damaged parts of the bone.

Aspect 11: The computing system of aspect 10, wherein the processing circuits are further configured to generate a revised surgical plan for the orthopedic revision surgery based on the second intra-revision model of the bone.

Aspect 12: The computing system of any of aspects 10-11, wherein the one or more processing circuits are further configured to: generate registration data that describes a spatial relationship between the intra-revision model of the bone and the bone; and generate, based on the registration data, a MR visualization that includes a virtual object defined by the revised surgical plan at a position that has a stable spatial relationship to the bone from a perspective of a user that perceives the MR visualization, wherein the virtual object provides information to the user about the orthopedic revision surgery.

Aspect 13: The computing system of any of aspects 10-12, wherein the intra-revision model of the bone is a second intra revision model of the bone and the one or more processing circuits are configured such that, as part of determining the damaged and intact parts of the bone, the one or more processing circuits: generate, based on the intra-revision imaging data, a first intra-revision model of the bone, wherein the first intra-revision model of the bone represents the intra-revision state of the bone during the orthopedic revision surgery after removal of the orthopedic prosthesis from the bone; and determine the damaged and intact parts of the bone based on the first intra-revision model of the bone.

Aspect 14: The computing system of aspect 13, wherein the one or more processing circuits are configured such that, as part of determining the damaged and intact parts of the bone, the one or more processing circuits: obtain a pre-morbid model of the bone; and for each region of the pre-morbid model of the bone: perform a comparison that compares the region of the pre-morbid model of the bone to a corresponding region of the first intra-revision model of the bone; determine, based on the comparison, whether the region contains bone in both the pre-morbid model of the bone and the first intra-revision model of the bone; and one of: determine that the region is one of the intact parts of the bone based the region containing bone in both the pre-morbid model of the bone and the first intra-revision model of the bone; or determine that the region is one of the damaged parts of the bone based on the region not containing bone in both the pre-morbid model of the bone and the first intra-revision model of the bone.

Aspect 15: The computing system of aspect 14, wherein the one or more processing circuits are configured to obtain the pre-morbid model of the bone comprises using Mean Statistical Shape (MSS) modeling to generate the pre-morbid model of the bone.

Aspect 16: The computing system of any of aspects 10-15, wherein: the one or more processing circuits are further configured to: obtain pre-revision imaging data of the bone, the pre-revision imaging data of the bone representing the pre-revision state of the bone; and generate, based on the pre-revision imaging data of the bone, data indicating a boundary between the orthopedic prosthesis and the bone, and the one or more processing circuits are configured such that, as part of determining the pre-revision model of the bone, the one or more processing circuits generate, based on the pre-revision imaging data and the data indicating the boundary of between the orthopedic prosthesis and the bone, the pre-revision model of the bone.

Aspect 17: The computing system of any of aspects 10-16, wherein the bone is one of: a scapula of the patient, a humerus of the patient, a fibula of the patient, a patella of the patient, a tibia of the patient, a talus of the patient, a hip of the patient, or a femur of the patient.

Aspect 18: The computing system of any of aspects 11-17, wherein the processing circuits are further configured to configure a robot to perform a surgical task based on the revised surgical plan for the orthopedic revision surgery.

Aspect 19: A computing system comprising means for performing the methods of any of aspects 1-9.

Aspect 20: A computer-readable data storage medium having instructions stored thereon that, when executed, cause a computing system to perform the methods of any of aspects 1-9.

While the techniques been disclosed with respect to a limited number of examples, those skilled in the art, having the benefit of this disclosure, will appreciate numerous modifications and variations there from. For instance, it is contemplated that any reasonable combination of the described examples may be performed. It is intended that the appended claims cover such modifications and variations as fall within the true spirit and scope of the invention.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and micro-wave, then the coaxial cable, fiber optic cable, twisted pair, DSL, or wireless technologies such as infrared, radio, and microwave are included in the definition of medium. It should be understood, however, that computer-readable stor-age media and data storage media do not include connec-tions, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Operations described in this disclosure may be performed by one or more processors, which may be implemented as fixed-function processing circuits, programmable circuits, or combinations thereof, such as one or more digital signal processors (DSPs), general purpose microprocessors, appli-cation specific integrated circuits (ASICs), field program-mable gate arrays (FPGAs), or other equivalent integrated or discrete logic circuitry. Fixed-function circuits refer to cir-cuits that provide particular functionality and are preset on the operations that can be performed. Programmable circuits refer to circuits that can programmed to perform various tasks and provide flexible functionality in the operations that can be performed. For instance, programmable circuits may execute instructions specified by software or firmware that cause the programmable circuits to operate in the manner defined by instructions of the software or firmware. Fixed-function circuits may execute software instructions (e.g., to receive parameters or output parameters), but the types of operations that the fixed-function circuits perform are gen-erally immutable. Accordingly, the terms "processor" and "processing circuitry," as used herein may refer to any of the foregoing structures or any other structure suitable for implementation of the techniques described herein.

Various examples have been described. These and other examples are within the scope of the following claims.

The invention claimed is:

1. A computer-implemented method for assisting an orthopedic revision surgery, the method comprising:
  obtaining, by one or more processors, a pre-revision model of a bone of a patient, the pre-revision model of the bone representing a pre-revision state of the bone after a prior orthopedic surgery on the bone and before the orthopedic revision surgery, wherein an orthopedic prosthesis was attached to the bone during the prior orthopedic surgery;
  obtaining, by the one or more processors, intra-revision imaging data of the bone, the intra-revision imaging data representing an intra-revision state of the bone during the orthopedic revision surgery after removal of the orthopedic prosthesis from the bone;
  determining, by the one or more processors, based on the intra-revision imaging data, damaged parts and intact parts of the bone, wherein the damaged parts of the bone are parts of the bone that are different in the intra-revision state of the bone from a pre-morbid state of the bone, and the intact parts of the bone are parts of the bone that are the same in the intra-revision state of the bone and the pre-morbid state of the bone; and
  generating, by the one or more processors, an intra-revision model of the bone by modifying the pre-revision model of the bone to exclude the damaged parts of the bone.

2. The computer-implemented method of claim 1, further comprising generating, by the one or more processors, a revised surgical plan for the orthopedic revision surgery based on the intra-revision model of the bone.

3. The computer-implemented method of claim 2, further comprising:
  generating, by the one or more processors, registration data that describes a spatial relationship between the intra-revision model of the bone and the bone; and
  generating, by the one or more processors, based on the registration data, a mixed reality (MR) visualization that includes a virtual object defined by the revised surgical plan at a position that has a stable spatial relationship to the bone from a perspective of a user that perceives the MR visualization, wherein the virtual object provides information to the user about the ortho-pedic revision surgery.

4. The computer-implemented method of claim 2, further comprising configuring, by the one or more processors, a robot to perform a surgical task based on the revised surgical plan for the orthopedic revision surgery.

5. The computer-implemented method of claim 1, wherein the intra-revision model of the bone is a second intra revision model of the bone and determining the dam-aged parts and the intact parts of the bone comprises:
  generating, based on the intra-revision imaging data, a first intra-revision model of the bone, wherein the first intra-revision model of the bone represents the intra-revision state of the bone during the orthopedic revision surgery after removal of the orthopedic prosthesis from the bone; and
  determining the damaged parts and the intact parts of the bone based on the first intra-revision model of the bone.

6. The computer-implemented method of claim 5, wherein determining the damaged parts and the intact parts of the bone comprises:
  obtaining a pre-morbid model of the bone; and
  for each region of the pre-morbid model of the bone:
    performing a comparison that compares the region of the pre-morbid model of the bone to a corresponding region of the first intra-revision model of the bone;
    determining, based on the comparison, whether the region contains bone in both the pre-morbid model of the bone and the first intra-revision model of the bone; and
    one of:
      determining that the region is one of the intact parts of the bone based the region containing bone in both the pre-morbid model of the bone and the first intra-revision model of the bone; or
      determining that the region is one of the damaged parts of the bone based on the region not contain-ing bone in both the pre-morbid model of the bone and the first intra-revision model of the bone.

7. The computer-implemented method of claim 6, wherein obtaining the pre-morbid model of the bone com-prises using Mean Statistical Shape (MSS) modeling to generate the pre-morbid model of the bone.

8. The computer-implemented method of claim 1, wherein:
  the method further comprises:

obtaining, by the one or more processors, pre-revision imaging data of the bone, the pre-revision imaging data of the bone representing the pre-revision state of the bone; and generating, by the one or more processors, based on the pre-revision imaging data of the bone, data indicating a boundary between the orthopedic prosthesis and the bone, and obtaining the pre-revision model of the bone comprises generating, based on the pre-revision imaging data and the data indicating the boundary between the orthopedic prosthesis and the bone, the pre-revision model of the bone.

9. The computer-implemented method of claim 1, wherein the bone is one of:

a scapula of the patient,
a humerus of the patient,
a fibula of the patient,
a patella of the patient,
a tibia of the patient,
a talus of the patient,
a hip of the patient, or
a femur of the patient.

10. A computing system for assisting an orthopedic revision surgery comprising:

a storage system configured to store a pre-revision model of a bone of a patient, the pre-revision model of the bone representing a pre-revision state of the bone after a prior orthopedic surgery on the bone and before the orthopedic revision surgery, wherein an orthopedic prosthesis was attached to the bone during the prior orthopedic surgery; and one or more processing circuits configured to:

obtain intra-revision imaging data of the bone, the intra-revision imaging data representing an intra-revision state of the bone during the orthopedic revision surgery after removal of the orthopedic prosthesis from the bone;

determine, based on the intra-revision imaging data, damaged parts and intact parts of the bone, wherein the damaged parts of the bone are parts of the bone that are different in the intra-revision state of the bone from a pre-morbid state of the bone, and the intact parts of the bone are parts of the bone that are the same in the intra-revision state of the bone and the pre-morbid state of the bone; and generate an intra-revision model of the bone by modifying the pre-revision model of the bone to exclude the damaged parts of the bone.

11. The computing system of claim 10, wherein the one or more processing circuits are further configured to generate a revised surgical plan for the orthopedic revision surgery based on the intra-revision model of the bone.

12. The computing system of claim 11, wherein the one or more processing circuits are further configured to:

generate registration data that describes a spatial relationship between the intra-revision model of the bone and the bone; and generate, based on the registration data, a mixed reality (MR) visualization that includes a virtual object defined by the revised surgical plan at a position that has a stable spatial relationship to the bone from a perspective of a user that perceives the MR visualization, wherein the virtual object provides information to the user about the orthopedic revision surgery.

13. The computing system of claim 11, wherein the one or more processing circuits are further configured to configure a robot to perform a surgical task based on the revised surgical plan for the orthopedic revision surgery.

14. The computing system of claim 10, wherein the intra-revision model of the bone is a second intra revision model of the bone and the one or more processing circuits are configured such that, as part of determining the damaged parts and the intact parts of the bone, the one or more processing circuits:

generate, based on the intra-revision imaging data, a first intra-revision model of the bone, wherein the first intra-revision model of the bone represents the intra-revision state of the bone during the orthopedic revision surgery after removal of the orthopedic prosthesis from the bone; and determine the damaged parts and the intact parts of the bone based on the first intra-revision model of the bone.

15. The computing system of claim 14, wherein the one or more processing circuits are configured such that, as part of determining the damaged parts and the intact parts of the bone, the one or more processing circuits:

obtain a pre-morbid model of the bone; and for each region of the pre-morbid model of the bone:

perform a comparison that compares the region of the pre-morbid model of the bone to a corresponding region of the first intra-revision model of the bone;

determine, based on the comparison, whether the region contains bone in both the pre-morbid model of the bone and the first intra-revision model of the bone; and one of:

determine that the region is one of the intact parts of the bone based the region containing bone in both the pre-morbid model of the bone and the first intra-revision model of the bone; or determine that the region is one of the damaged parts of the bone based on the region not containing bone in both the pre-morbid model of the bone and the first intra-revision model of the bone.

16. The computing system of claim 15, wherein the one or more processing circuits are configured to obtain the pre-morbid model of the bone comprises using Mean Statistical Shape (MSS) modeling to generate the pre-morbid model of the bone.

17. The computing system of claim 10, wherein:

the one or more processing circuits are further configured to:

obtain pre-revision imaging data of the bone, the pre-revision imaging data of the bone representing the pre-revision state of the bone; and generate, based on the pre-revision imaging data of the bone, data indicating a boundary between the orthopedic prosthesis and the bone, and the one or more processing circuits are configured such that, as part of determining the pre-revision model of the bone, the one or more processing circuits generate, based on the pre-revision imaging data and the data indicating the boundary of between the orthopedic prosthesis and the bone, the pre-revision model of the bone.

18. The computing system of claim 10, wherein the bone is one of:

a scapula of the patient,
a humerus of the patient,
a fibula of the patient,
a patella of the patient,
a tibia of the patient,
a talus of the patient, a hip of the patient, or a femur of the patient.

19. A non-transitory computer-readable data storage medium having instructions stored thereon that, when executed, cause a computing system to:

obtain a pre-revision model of a bone of a patient, the pre-revision model of the bone representing a pre-revision state of the bone after a prior orthopedic surgery on the bone and before an orthopedic revision surgery, wherein an orthopedic prosthesis was attached to the bone during the prior orthopedic surgery;

obtain intra-revision imaging data of the bone, the intra-revision imaging data representing an intra-revision state of the bone during the orthopedic revision surgery after removal of the orthopedic prosthesis from the bone;

determine, based on the intra-revision imaging data, damaged parts and intact parts of the bone, wherein the damaged parts of the bone are parts of the bone that are different in the intra-revision state of the bone from a pre-morbid state of the bone, and the intact parts of the bone are parts of the bone that are the same in the intra-revision state of the bone and the pre-morbid state of the bone; and generate an intra-revision model of the bone by modifying the pre-revision model of the bone to exclude the damaged parts of the bone.

20. The non-transitory computer-readable data storage medium of claim 19, wherein the intra-revision model of the bone is a second intra revision model of the bone and the instructions that cause the computing system to determine the damaged parts and the intact parts of the bone comprise instructions that, when executed, cause the computing system to:

generate, based on the intra-revision imaging data, a first intra-revision model of the bone, wherein the first intra-revision model of the bone represents the intra-revision state of the bone during the orthopedic revision surgery after removal of the orthopedic prosthesis from the bone; and determine the damaged and intact parts of the bone based on the first intra-revision model of the bone.

* * * * *